US010046038B2

(12) United States Patent
Smits et al.

(10) Patent No.: US 10,046,038 B2
(45) Date of Patent: Aug. 14, 2018

(54) LEPTOSPIRA WITH INCREASED ANTIGENIC MASS

(71) Applicant: Intervet Inc., Madison, NJ (US)

(72) Inventors: Christian Theodoor Gerardus Smits, Boxmeer (NL); Edwin Kets, Boxmeer (NL); Henriette Adriaanse, Boxmeer (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/650,720

(22) PCT Filed: Dec. 20, 2013

(86) PCT No.: PCT/EP2013/077590
§ 371 (c)(1),
(2) Date: Jun. 9, 2015

(87) PCT Pub. No.: WO2014/096311
PCT Pub. Date: Jun. 26, 2014

(65) Prior Publication Data
US 2015/0306199 A1    Oct. 29, 2015

(30) Foreign Application Priority Data

Dec. 21, 2012 (EP) .................... 12199264

(51) Int. Cl.
| | | |
|---|---|---|
| *A61K 39/02* | (2006.01) | |
| *C12N 1/20* | (2006.01) | |
| *C12R 1/01* | (2006.01) | |
| *C12N 1/38* | (2006.01) | |
| *A61K 39/00* | (2006.01) | |

(52) U.S. Cl.
CPC ...... *A61K 39/0208* (2013.01); *A61K 39/0225* (2013.01); *C12N 1/20* (2013.01); *C12N 1/38* (2013.01); *C12R 1/01* (2013.01); *A61K 2039/521* (2013.01); *Y02A 50/48* (2018.01)

(58) Field of Classification Search
None
See application file for complete search history.

(56) References Cited

FOREIGN PATENT DOCUMENTS

| | | | |
|---|---|---|---|
| RU | 1538305 C | * | 12/1994 |
| WO | 2006113601 A2 | | 10/2006 |

OTHER PUBLICATIONS

Tween 80/ Polysorbate 80 retrieved from https://www.avantormaterials.com/commerce/product.aspx?id=2147508513 on Feb. 29, 2016.*
National Center for Biotechnology Information. PubChem Compound Database; CID=5280934, https://pubchem.ncbi.nlm.nih.gov/compound/5280934 (accessed Mar. 16, 2017).*
Vegetable Oils. PROTA Foundation/Backhuys Publishers/CTA, Wageningen, Netherlands, 2007, pp. 50-52 and pp. 108-110.*
γ-Linolenic Acid: Recent Advances in Biotechnology and Clinical Applications. Huang, Y and Ziboh, VA, Eds. AOCS Press, Champain, Illinois, 2000, p. 1-3 (hereinafter "γ-Linolenic Acid").*
Johnson, R.C. and Gary, N.D., Nutrition of Leptospira Pomona II. Fatty Acid Requirements, J. Bacteriol., 1962, pp. 976-982, vol. 85.
Hennig, B. and Watkins, B.A., Linoleic acid and linolenic acid: effect on permeability properties of cultured endothelial cell monolayers 1-3, Am J Clin Nutr, 1989, pp. 301-305, 49.
Johnson, R.C. and Harris, V.G., Differentiation of Pathogenic and Saprophytic Leptospires, Journal of Bacteriology, Jul. 1967, pp. 27-31, vol. 94, No. 1.
Ruby, K.W. et al., Assay for Measuring Relative Potency of Leptospiral Bacterins Containing Serovar Pomona, Biologicals, 1992, pp. 259-266, 20.
Schoone, G.J. et al., An Immunoprotective Monoclonal Antibody Directed against Leptospira interrogans serovar copenhageni, Journal of Genral Microbiology, 1989, pp. 73-78, 135.
Stern, N. et al., Studies on the Metabolism of Fatty Acids in Leptospira: The Biosynthesis of Δ9- and Δ11-Monounsaturated Acids, European J. Biochem., 1969, pp. 101-108, 8.
Bey, F.R. and Johnson, R.J., Protein-free and low-protein media for the cultivation of Leptospira, Infection and Immunity, Sep. 6, 1977, pp. 562-569, vol. 19, No. 2.
Ellinghausen, H.C. et al., Nutrition of Leptospira pomona and growth of 13 other serotypes: fractionation of oleic albumin complex and a medium of bovine albumin and polysorbate 80, Am J Vet Res, Jan. 1965, pp. 45-51, Vo.. 26, No. 110.
European Search Report for 12199264.8, dated May 6, 2013, 8 pages.
González A. et al., Modified EMJH medium for cultivation of Leptospira interrogans serogroup ballum, REV Argent Microbiol, 2006, pp. 61-68, vol. 38, No. 2.
International Search Report for PCT/EP2013/077590, dated Apr. 3, 2014, 12 pages.
Johnson, R.C. et al., Lipids of parasitic and saprophytic leptospires, Infection and Immunity, Jun. 1, 1970, pp. 286-291, vol. 2. No. 3.
Mickle, T.R., A physical, cultural, and nutritional study of leptospira interrogans serotype hardjo with emphasis on antigenicity, immunogenicity and viability, Thesis presented to the school of graduate studies Drake University, Aug. 1983, pp. 1-119.
Priya S Mir et al., Conjugated linoleic acid-enriched beef production, Am J Clin Nutr, 2004, pp. 1207S-1211S, XP055060752.
Stalheim, et al., Cultivation of Leptospirae, Journal of Bacteriology, 1964, pp. 48-54, vol. 88, No. 1.
Stalheim, O.H.V. et al., Antigenicity and immunogenicity of leptospires grown in chemically characterized medium, Am J Vet Res, Jul. 1964, pp. 1277-1280, vol. 25, No. 107.

(Continued)

*Primary Examiner* — Oluwatosin A Ogunbiyi

(57) ABSTRACT

The antigenic mass of *Leptospira* cultures can be significantly increased, independent from any increase in biomass, by supplementing *Leptospira* cultures with a specific type of fatty acid: a polyunsaturated C18 fatty acid. This provides advantages in the production *Leptospira* antigens. Also this enables the production of improved Leptospirosis vaccines, that are safer and more effective.

17 Claims, 20 Drawing Sheets

(56) References Cited

OTHER PUBLICATIONS

Figure 1:
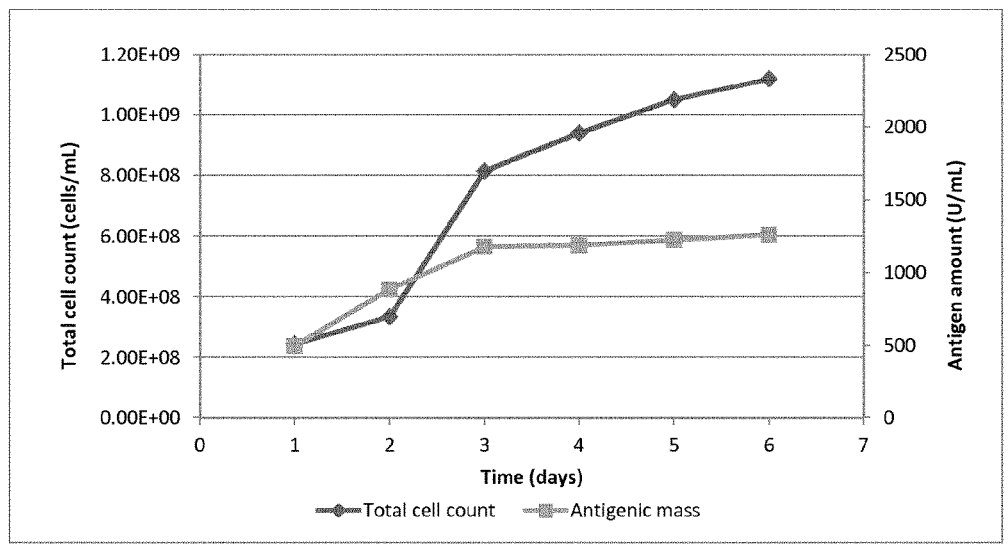

Staneck, J.L. et al., Growth requirements of pathogenic leptospira, Infection and Immunity, Mar. 7, 1973, pp. 886-897, vol. 7, No. 6.
Verma A.K. et al., Leptospirosis-persistence of a dilemma: an overview with particular emphasis on trends and recent advances in vaccines and vaccination strategies, Pakistan Journal of Biological Sciences, 2012, pp. 954-963, vol. 15, No. 20.
Wang, Zhijun et al., Leptospirosis vaccines, Microbial cell factories, Dec. 11, 2007, p. 39, vol. 6, No. 1.

* cited by examiner

LEPTOSPIRA WITH INCREASED ANTIGENIC MASS

CROSS-REFERENCE TO RELATED APPLICATIONS

This application is a national stage entry under 35 U.S.C. § 371 of PCT/EP2013/077590, filed on Dec. 20, 2013, which claims priority to EP application No. EP12199264.8filed on Dec. 21, 2012. The content of PCT/EP2013/077590 is hereby incorporated by reference in its entirety.

The current invention generally relates to the fields of bacteriology, and to bacterial vaccines. In particular the invention relates to a method for increasing the antigenic mass of *Leptospira*, to the *Leptospira* obtainable by that method, and to vaccines and uses of such *Leptospira*.

The spirochete bacteria of the genus *Leptospira* belong to the family of Leptospiraceae, and the phylum Spirochaetes. *Leptospira* are Gram negative, aerobic, motile bacteria, with an elongated, thin, and spiral-shaped form. Pathogenic *Leptospira* are found worldwide in many types of animals as well as in humans; mammals, such as rodents, wildlife, farm animals, and dogs are the natural reservoirs. The bacteria cause a disease called Leptospirosis, or: Weil's disease. This develops when *Leptospira*—after infection and transport via the bloodstream—invade all internal organs, and may display a wide range of mild to severe symptoms, even to mortality, and is of an acute or chronic nature. This variability is the reason the disease is often misdiagnosed. Main symptoms are: fever, nausea, and jaundice, resulting from vasculitis leading to renal-, liver-, or pulmonary failure or cardiovascular disease. The *Leptospira* typically survive in the renal or genital tract of a host, and this way cause horizontal spread which may also give rise to zoonosis, whereby humans become infected from contact with animal urine or with contaminated surface water. For a review, see: P. Levett, 2001 (Clin. Micr. Rev., vol. 14, p. 296). *Leptospira* are quite stable in nature, and can survive for months under aqueous conditions and at ambient temperatures.

The classification of *Leptospira* can be confusing with different systems being used: for many years the classification was based on a serologic differentiation, whereby all pathogenic *Leptospira* are indicated as serovars of the species *Leptospira interrogans* (sensu lato). In this system, serovars are distinguished by serological testing of the bacteria's main immunogen: the lipopolysaccharide (LPS) on its outer membrane. Currently more than 200 serovars have been described, which are combined into some 25 serogroups.

However, perpendicular to this classification by serotyping, exists a system of genotyping based on molecular biological features, into so-called: genomospecies. In practice, one *Leptospira* genomospecies can comprise several serovars, and vice versa. For the present case the serologic classification into serovars will be used.

Some *Leptospira* serovars infect only a specific host species, but most serovars have a wide host range. For example: *L. interrogans* (sensu lato) serovar Hardjo is associated with infection of bovines, and in swine serovars Tarassovi, Pomona and Bratislava are most often incriminated. However, serovars such as Canicola, lcterohaemorrhagiae, Bratislava and Grippotyphosa can infect swines, canines, and humans.

Detection of Leptospiral infection of a host is possible in a variety of ways. The gold standard is the serologic detection of specific antibodies in a host's serum by the so-called: microscopic agglutination test (MAT). In this test a serial dilution of a patient's serum is incubated with live *Leptospira* of a specific serovar. When specific antibodies are present in the serum, these will agglutinate the test bacteria, which can be read e.g. by (dark-field) microscope. The test is highly specific, and the MAT is also decisive for the sero-classification of *Leptospira* isolates. Alternative tests are Elisa (enzyme linked immunosorbent assay), or PCR (polymerase chain reaction).

Treatment of Leptospirosis can be done therapeutically by administration of antibiotics. However, because the disease is frequently misdiagnosed, prophylaxis by vaccination is preferred. Several types of vaccines against *Leptospira* for animal—or human use are under investigation, but currently only veterinary vaccines are widely available commercially. The species of animals that are routinely vaccinated are pigs, cattle, and dogs. Vaccination then serves both to prevent disease of the host, as well as to reduce zoonotic spread.

Current Leptospirosis vaccines are based on a suspension of inactivated whole bacterial cells, a so-called bacterin, of a strain from a relevant serovar. These vaccines induce an effective immunity of the humoral type, whereby most immuno-protective antibodies are able to agglutinate and thus neutralise *Leptospira*. The bacteria's immunodominant antigen is the LPS, and specifically: epitopes on oligosaccharide moieties of the LPS. The immunity induced is mainly serovar specific, with some cross-protection among related serovars, for example from within the same serogroup. An example of a Leptospirosis vaccine is: Leptavoid® H (MSD Animal Health), for bovines, comprising a bacterin from a strain of *L. interrogans* (sensu lato) serovar Hardjo.

However, as most field situations show prevalence of *Leptospira* from more than one serogroup, therefore many commercial Leptospirosis vaccines are combination vaccines which provide broad protection. An example is the canine vaccine: Nobivac® Lepto4 (Merck Animal Health), which comprises strains from each of the *L. interrogans* (sensu lato) serogroups: Canicola, Grippotyphosa, Icterohaemorrhagiae and Pomona. Also, Leptospirosis vaccines are often combined with other bacterial—or with viral vaccine compounds.

Today *Leptospira* are routinely being proliferated in in vitro cultures, for research—or diagnostic purposes, but mainly for the production of vaccines. Methods and procedures for the in vitro proliferation of *Leptospira* have been known for over 50 years, and so are the ingredients that are critical for its relatively simple culture medium. In the 1960's it was established that *Leptospira* (for in vitro proliferation) require long-chain fatty acids for their nutrition and cellular composition. Also that these long-chain fatty acids are used as the sole source of energy and carbon, as there is no (detectable) consumption of proteins or carbohydrates from the culture medium. Therefore these fatty acids needed to be provided by the culture medium as *Leptospira* cannot synthesize long-chain fatty acids de novo, nor extend short-chained fatty acids. These insights helped to develop a semi-defined synthetic *Leptospira* culture medium (Johnson & Gary 1963; Stalheim & Wilson 1964), in which the previous use of up to 10% v/v of whole (rabbit) serum, was replaced by a combination of an albumin fraction and a defined source of fatty acid. This was further developed into the synthetic medium that is still in use today as the standard culture medium for small-or large scale in vitro proliferation of *Leptospira*: the EMJH medium, as developed by Ellinghausen and McCullough (1965, Am. J.

of Vet. Res., vol. 26, p. 45), and modified by Johnson and Harris (1967, J. of Bacteriol., vol. 94, p. 27).

The EMJH medium contains next to essential vitamins, salts and minerals, also 0.125% v/v polysorbate 80, and 1% w/v bovine serum albumin (BSA) (Faine, S., 1994, p. 312, in: Leptospira and Leptospirosis, ed. S. Faine, Boca Raton, Fla., USA, CRC Press).

Polysorbate 80, which is best known by one of its commercial product names: Tween® 80 (ICI Americas, Inc.), is: polyoxyethylene (20) sorbitan monooleate (CAS nr. 9005-65-6). Polysorbate 80 is a non-ionic surfactant that is used extensively as an emulsifier and solubiliser in pharmaceuticals, cosmetics and foods (E 433). In the EMJH medium however it serves as the bacteria's source of long-chain fatty acids, as it conveniently is water-soluble and has a relatively low toxicity for the bacteria. The main component at about 70% v/v of polysorbate 80 is oleic acid (C18:1), but some other fatty acids are also present, mainly: palmitic acid (C16:0), and palmitoleic acid (C16:1), although this is batch—and manufacturer dependent.

In this respect: the designation of fatty acids such as oleic acid as: "C18:1", is according to the C:D notation, which is a well-known standard shorthand which describes a fatty acid by its main characteristics: the number of carbon atoms in the acyl chain (for oleic acid: 18), and the number of double (unsaturated) bonds (for oleic acid: 1).

As Leptospira in vitro do not consume protein, the main function of the albumin component of EMJH is considered to be the detoxification of the fatty acids in the culture medium that are provided by the polysorbate 80, by reversibly complexing them, while keeping them biologically available.

Serum albumin, next to providing osmotic pressure, is an important transporter protein in the blood for a variety of compounds, such as proteins, lipids, vitamins, small molecules, etc.

Lipids bound to serum albumin contain di-and tri-glycerides, and esters of cholesterol and phospholipids, but most of it (>90%) is in the form of free fatty acids; with "free" meaning: non-esterified, or not covalently linked. Of these free fatty acids bound to albumin, more than 90% are midsize-and long-chain fatty acids in the range of C14-C20, mainly: myristic acid (C14:0), palmitic acid (C16:0), palmitoleic acid (C16:1), stearic acid (C18:0), oleic acid (C18:1), linoleic acid (C18:2), and arachidonic acid (C20:4).

Albumins reversibly bind these fatty acids on several binding sites with different affinity. How much, and which type of fatty acid is bound to an albumin sample from a donor, has a wide physiological variation, and is dependant from chemical features of the fatty acid, such as chain length and level of unsaturation, but also on biological features from the donor of the albumin, such as: species, breed, and gender, as well as its nutritional-and activity status.

For commercial BSA's the amount and the type of fatty acids bound are dependent on the production protocol used by a manufacturer, and vary for each batch.

Classical albumin preparations were obtained by a cold-ethanol fractionation (Cohn et al., 1946, J. of the Amer. Chem. Soc., vol. 68, p. 459) to yield the so-called: Cohn fraction V albumin product.

Since then, a wide variety of serum albumin types and-qualities for use e.g. in biochemistry and tissue culture has become available commercially. An extensive review of the variability of serum albumin was made by Janatova (1974, J. of Medicine, vol. 5, p. 149).

Although under experimental conditions more than 10 molecules of fatty acid could be bound per molecule of albumin (Spector & Hoak, 1969, Anal. Biochem., vol. 32, p. 297), physiologically albumin will carry between about 0.3 and 3 mole fatty acid per mole albumin (Hennig & Watkins, 1989, Am. J. of Clin. Nutr., vol. 49, p. 301).

Commercial serum albumins with low amounts of fatty acids, i.e. below 0.1 mole fatty acid/mole albumin, are also available; such albumin products have deliberately been de-lipidated using one of a variety of available techniques, such as extraction with an organic solvent and/or adsorption to charcoal. However, to obtain very low lipid load levels requires aggressive extraction methods at very low pH value, which may result in denaturation of the albumin.

Large amounts of serum albumins for use in industrial scale biological processes, effectively are only commercially available from bovines, as by-product from the meat industry.

Of the different kinds of BSA suitable for use in in vitro cell-proliferation, some are recommended for use with a specific cell-type. One example is BovoLep® BSA (Bovogen, Australia), which is recommended for promoting the growth of Leptospira in culture; this is a standard BSA that was enriched with a number of vegetable fatty acids.

The complete EMJH culture medium then provides all the fatty acids that are known to be critical for the proliferation of Leptospira in culture: palmitic acid (C16:0), stearic acid (C18:0) and oleic acid (C18:1) (Johnson & Gary, 1963, supra).

This EMJH medium allows proliferation of most of the relevant serovars of L. interrogans (sensu lato). Typical conditions for industrial scale proliferation of Leptospira are at 28-30° C., with control of $pO_2$ and pH, in a standard fermenter vessel with stirrer. Nevertheless, Leptospira proliferate relatively slowly: generation times between 12 and 24 hours have been reported, depending on the virulence, and level of adaptation to in vitro proliferation conditions. As a result: to reach a high biomass the proliferation process takes relatively long, typically 4-7 days, depending on inoculation density, and it takes several pre-cultures to prepare sufficient inoculum. This poses a heavy burden on the fermenter capacity of a producer. Also, this extended culture time poses a great risk for a contamination to develop, e.g. by bacteria, yeast, or fungi that have much shorter doubling times.

Consequently, there is a need for improved methods for the production of Leptospira antigens in in vitro cultures.

The literature in the field describes some efforts to improve the proliferation of *Leptospira* in in vitro cultures. Some adaptations of the EMJH medium have re-introduced serum, or added a further polysorbate, and/or a hydrolysate. However such enriched EMJH media are not generally used in large scale in vitro proliferation of *Leptospira*, but are used in diagnostics, typically as semi-solid media, to detect and proliferate even low amounts of the most demanding *Leptospira* strains from clinical specimens.

Typically *Leptospira* are proliferated in vitro to prepare an inactivated Leptospirosis vaccine. After the proliferation phase, the downstream process generally starts by the inactivation of the final culture product, to produce the bacterin. This can be done in several ways, commonly by chemical inactivation, such as with formalin, thiomersal, betapropiolactone (BPL), or beta-ethanolamine (BEA). A next step often is to concentrate and purify the inactivated culture, e.g. by centrifugation or filtration. The resulting antigen preparation is then formulated into a vaccine.

It is common practice to formulate inactivated Leptospirosis vaccines based on biomass, whereby one animal dose is made to contain a certain number of cells, typically about 10^9 cells/dose, of a particular serovar. However this cell count cannot be made on the formulated final product, as the (chemical) inactivation damages the bacterial cells. Therefore, the cell number is determined from the final culture, before its inactivation, by counting all intact cells (alive and dead). With this number, it is calculated how many doses/ml can be allotted to the final product after formulation. As a quality control check for the release of the product to the market, the immunological efficacy (a.k.a. the potency) of the final vaccine is verified. The batch potency test currently required by the regulatory authorities is an in vivo assay employing vaccination and challenge in hamsters (e.g. European Pharmacopeia monograph 0447, for a Canine Leptospirosis vaccine).

An in vitro potency test for Leptospirosis vaccine is known (Ruby et al., 1992, Biologicals, vol. 20, p. 259). This is based on quantifying the antigenic mass of the final vaccine by serological assay, using serovar specific antibodies and-standards. Although the correlation between antigenic mass of *Leptospira* bacterin and immunological potency is well known, the formulation of Leptospirosis vaccines is still based on biomass/dose.

A consequence of preparing *Leptospira* bacterin vaccines based on biomass, is that such a vaccine dose comprises an amount of protein and other bacterial components that hardly contribute to immunisation-as does LPS-, but on the contrary may lead to adverse local and/or systemic vaccination reactions. This problem is exacerbated in the case of vaccines that combine several Leptospiral antigens. In an attempt to improve the safety of Leptospirosis vaccines, additional purification steps in the downstream process are generally applied. A fear of adverse vaccination reactions is also the main reason that no bacterin-based Leptospirosis vaccine for use in humans is generally available to date.

To overcome possible vaccination reactions, some groups have tried to reduce the burden of non-protective and medium-derived vaccine components of a (combined-) Leptospirosis vaccine, by applying adapted media for the *Leptospira* culture which are low in protein or even protein-free. However, these media must still provide the essential long-chain fatty acids that are required to support *Leptospira* proliferation. This required a solution for dealing with the inherent toxicity of these fatty acids, as now these could no longer be detoxified by a bulk of protein such as provided by serum or BSA. One approach was to detoxify the polysorbate itself, e.g. by ion-exchange, or by extraction with polyvinylpyrrolidone, or charcoal (Bey & Johnson, 1978, Inf. & Imm., vol. 19, p. 562). An alternative approach is described in WO 2006/113.601, where the toxicity of the fatty acids is limited by supplementing a protein-free culture medium with polysorbate in repeated small quantities, a so-called fed-batch culture process, based on an increase of the biomass at a controlled, submaximal growth rate.

Until today no commercial Leptospirosis vaccines based on protein-free cultured *Leptospira* are commercially available, and conventional vaccines still rely on downstream purification.

Nevertheless, none of these prior art studies reported any effect of the alterations to the culture medium, or to the conditions for proliferation, on the antigenic mass and/or the immunogenicity of the *Leptospira* produced. Therefore all these in essence are alternative methods for the production of *Leptospira* biomass.

It is therefore an object of the present invention to provide improvements to the production of *Leptospira* antigenic mass and provide improved vaccines resulting therefrom.

Surprisingly it was found that this object can be met, and the disadvantages of the prior art can be overcome, by supplementing a culture of *Leptospira* with a specific long-chain unsaturated fatty acid: a polyunsaturated C18 fatty acid. This leads to a rapid and strong increase of the antigenic mass which exceeds any increase in biomass up to 3 fold.

This discovery opens the way to a number of advantageous utilities, such as to generation of *Leptospira* with increased antigenic mass, which can be used for the production of improved vaccines against Leptospirosis. Because the increase in antigen amount was found to exceed the increase in biomass, therefore there is a net increase of the antigen amount per set amount of bacterial cells, when comparing a supplemented-to a non-supplemented *Leptospira* culture.

*Leptospira* that have such an increased antigenic mass, can now be used to prepare vaccines that have the same antigen content as in prior art vaccines, but with a reduced amount of other bacterial-and culture-derived components. This is favourable for the downstream processing, and for the level of vaccination side-effects. Alternatively: vaccines with an increased antigenic mass can now be applied, at the same level of non-specific components as previously. Next to being favourable for the safety of the vaccinated target, it will be apparent to a skilled person that all these improvements also are highly relevant in economic terms.

Further, polyunsaturated C18 fatty acid-supplemented *Leptospira* cultures now reach a prior art level of antigenic mass several days earlier than previously. Therefore such cultures can now be produced quicker, more economical, and with lesser chance of contaminations, as culture times can now be considerably reduced. Alternatively: if polyunsaturated C18 fatty acid-supplemented *Leptospira* cultures are allowed to proliferate to a maximal biomass as previously, much increased amounts of antigen can now be harvested.

The present invention enables the improvement of existing culture media for *Leptospira* proliferation and antigen production, and the rational design of optimal (semi-)synthetic media.

For supplementing a *Leptospira* culture with a polyunsaturated C18 fatty acid, compounds and/or compositions can be used that are either pure or relatively rich in polyunsaturated C18 fatty acid; an economical example are vegetable oils.

In addition, because in *Leptospira* the processes for production of biomass, and for generation of LPS antigen seem to be separate to a large extent, an uncoupled process-design is now conceivable wherein in an initial stage a high amount of *Leptospira* biomass is produced, and in a separate, later stage, the *Leptospira* are induced to produce LPS antigen by supplementing them with a polyunsaturated C18 fatty acid. The separation of these two steps then allows for both processes to be separately optimised for their different relevant parameters, such as length of incubation, incubation temperature, etc. This also provides several logistical-and planning advantages, for example by allowing intermediate storage, harvesting and/or purification.

All this was totally unexpected, as polyunsaturated C18 fatty acids are hardly ever mentioned in the prior art in relation to *Leptospira* proliferation conditions: Stern et al. (1969, Eur. J. of Biochem., vol. 8, p. 101) described that *Leptospira* incorporate linoleic acid (C18:2) from the culture medium into its cellular membrane lipids. Johnson et al. (1970, Inf. & Imm., vol. 2, p. 286) reported that linoleic acid was one of a list of fatty acids that were present in BSA that was used for proliferating *Leptospira* cultures, but did not provide specific amounts. Hardly any publication mentions a linolenic acid (C18:3) in relation to *Leptospira* culture, and never as beneficial. Consequently, no items of prior art describe a polyunsaturated C18 fatty acid to be of any special relevance for *Leptospira*, except for its potential toxicity. Linoleic or linolenic acid were never mentioned or suggested to be of special relevance for the generation of *Leptospira* antigen, specifically of LPS antigen.

On the contrary, the consensus in the prior art in this field is that the relevant fatty acids for *Leptospira* are palmitic-, stearic-, and oleic acids, and that these are all provided in abundance in standard culture medium by polysorbate 80. This way *Leptospira* with an 'adequate' amount of LPS antigen have been produced for many years, and no attempts have been described or suggested to improve the amount of LPS antigen per unit of *Leptospira* biomass. There was also no incentive to do so, as Leptospirosis vaccines are routinely formulated based on biomass, therefore maximising the number of *Leptospira* cells in a culture has always been the main focus in this field, not their antigenic mass.

It is not known why *Leptospira* require polyunsaturated C18 fatty acids for the production of their LPS antigen, nor in what way a polyunsaturated C18 fatty acid is used by *Leptospira* to generate (part of) the LPS molecule.

Although the inventors do not want to be bound by any theory or model that might explain these observations, the inventors now speculate that in *Leptospira* the biological processes directed to bacterial proliferation, and those directed to the generation of LPS may rely on partly separate enzyme systems, requiring different nutrients. This aside from the fact that supplementation with a polyunsaturated C18 fatty acid may also induce some increase of biomass.

The inventors further speculate that the standard *Leptospira* culture media currently in use, such as EMJH, only contain an amount of polyunsaturated C18 fatty acids that is suboptimal for the efficient generation of *Leptospira* antigen; this is independent of the fact that such media do provide an abundance of the fatty acids that are required for the formation of *Leptospira* biomass. Consequently, in these prior art *Leptospira* culture media the polyunsaturated C18 fatty acid is rapidly depleted, after which antigen production comes to a halt long before the maximal cell number is reached. This makes that only a part of the capacity of the *Leptospira* to produce LPS antigen has so far been used.

Therefore in one aspect the invention provides a method for increasing the antigenic mass of a *Leptospira* culture, the method comprising the step of supplementing said *Leptospira* culture with a polyunsaturated C18 fatty acid.

The "antigenic mass" for the invention is the amount of LPS antigen of a fixed number of *Leptospira* cells, which can be determined in a serological assay, such as an Elisa. It is expressed herein as a specific antigenic mass: the amount of immunodominant protective antigenic epitopes on the LPS of a fixed number of *Leptospira* cells, and presented as the number of serological units of Leptospiral LPS antigen per $1 \times 10^9$ *Leptospira* cells.

The *Leptospira* cells are counted according to common procedures, before inactivation, and counting all whole cells, alive or dead; this is what is understood as "biomass" for the invention.

Consequently, for the invention the antigenic mass of a *Leptospira* culture increases when the amount of antigen per *Leptospira* cell increases, as a result from applying a method according to the invention.

This is opposed to the effect in prior art methods for producing *Leptospira* antigens by proliferating *Leptospira*; these focussed on increasing *Leptospira* biomass, but did not improve the amount of antigen per cell. Consequently, when the biomass increases and the antigen amount does not, that causes a decrease in the ratio of antigen amount/unit of biomass.

Antigenic mass is a well-known term in the field, and is typically determined using a serological assay, such as an Elisa, using antibodies that are specific for the measured antigen, here: *Leptospira* LPS. The amount of antigen detected in a sample is then expressed in a number of arbitrary units, whereby these units are defined by reference to the amount of antigen in a standard sample, which is for example set to contain 1000 units. Consequently, the absolute value of the score of an antigen amount is arbitrary, as it is dependent on the specific test applied, and the antibodies and the reference sample that were used. What matters however is the relative difference between the scores of samples tested under the same conditions, and against the same reference sample. This can for example be expressed as the difference in antigen amount measured (e.g. 250 versus 500 Antigen units/ml), or can conveniently be expressed as a percentage. Such a percentage of difference between two samples will also apply when the same two samples are analysed with a different antibody or against a different (but appropriate) reference sample.

The preferred assay for determining antigen amount for use in the invention is an Elisa, which uses antibodies that are specific for the LPS antigen of a particular *Leptospira* serogroup or serovar. Such antibodies can agglutinate *Leptospira* in a MAT. Preferably the antibodies are monoclonal antibodies, and the sample is of sufficiently high titre to allow it to be used in dilution.

Protocols and materials for performing an antigenic mass assay for *Leptospira* have been well known to a skilled person for a long time, are generally available, and are described and exemplified herein in detail. For example, public biological resource centres such as the ATCC (Manassas, Va., USA), or the CNCM (Institut Pasteur, Paris, France) can provide *Leptospira* bacteria of most serovars, and provide mouse hybridoma cell-lines expressing serovar specific and agglutinating monoclonal antibodies, or their monoclonals, see: Schoone et al. (1989, J. of Gen. Microbiol., vol. 135, p. 73).

Alternatively such materials can routinely be produced in house using standard techniques: bacteria can be obtained from infected humans or animals (applying proper biosafety measures), and these can be characterised using common techniques; the antigen can be produced by proliferating *Leptospira* using routine techniques; also serovar specific antibodies can be obtained by immunisation of experimental animals, and methods to produce monoclonal antibodies are well known. The skilled person can easily determine the specificity and titre of these antibodies e.g. by performing the well-known MAT.

Also, several governmental institutions and international organisations provide reference samples of *Leptospira* bacteria,-antigens, and specific antibodies e.g. for assay development. For example the Royal Tropical Institute (Amsterdam, the Netherlands), which is a reference centre for *Leptospira* for the WHO, FAO and OIE. Also, the USDA (Ames, Iowa, USA) provides standard reference bacterins of the major *Leptospira* serovars, and supports interested parties with protocols and materials for setting up and performing antigen amount (potency) ELISA's.

Otherwise, the development and/or the routine performance of *Leptospira* antigen amount assays can be outsourced to one of many (commercial) diagnostic service institutions.

For the invention, "increasing the antigenic mass" has been achieved by a method according to the invention, if a higher antigenic mass is found for a polyunsaturated C18 fatty acid-supplemented *Leptospira* culture, when compared to the antigenic mass of the same or a similar *Leptospira* culture that was not supplemented with a polyunsaturated C18 fatty acid, under otherwise identical conditions. An increase in antigenic mass with 20% can already be detected with statistical significance using routine techniques, well known to the skilled artisan.

Therefore, in a preferred embodiment of a method according to the invention, the increase in the antigenic mass of a *Leptospira* culture is with at least 20%, as compared to the antigenic mass of a similar *Leptospira* culture that was not supplemented with a polyunsaturated C18 fatty acid.

More preferably the increase in antigenic mass is with at least 25, 28, 30, 35, 40, 45, 50, 63, 77, 90, 100, 121, 150, 175, 184, or with at least 200%, in that order of preference.

For the invention, "a similar *Leptospira* culture" refers to a culture of *Leptospira* that in biologic terms is highly comparable to the culture of *Leptospira* that it is compared with. For example this could refer to the use of a *Leptospira* culture from the same isolate, strain or serogroup for making this comparison.

Examples of an increases of the antigenic mass per unit biomass (as compared to similar non-supplemented cultures) for different *Leptospira* serogroups that were observed by the inventors relative to similar but non-supplemented cultures, following application of a method according to the invention, were: for lcterohaemorrhagiae an increase with: 164%, for Sejroe (serovar Hardjo): 184%, for Grippotyphosa: 63%, for Tarassovi: 141%, for Pomona: 73%, for Canicola: 118%, and for Australis (serovar Bratislava): 62%. Details are provided in the Examples and Figures. The differences in effect may be *Leptospira* serogroup specific, or may be related to the characteristics of the specific strain-material that was used from that serovar. Nevertheless, all these increases are highly relevant economically.

It is well within the routine capabilities of the skilled person to optimise the increase in antigenic mass resulting from supplementation with a polyunsaturated C18 fatty acid as in a method according to the invention, e.g. by adaptation of the conditions of the culture, of the supplementation, or of the *Leptospira* used.

This insight now allows the further optimisation of cultures of *Leptospira* from the different serogroups, by supplementation with a particular polyunsaturated C18 fatty acid, in order to obtain a maximal relative increase in the antigenic mass/biomass ratio of that *Leptospira* serogroup, serovar, type, or strain.

Therefore in preferred embodiments of the method according to the invention:
for a culture of *Leptospira* serogroup lcterohaemorrhagiae, the polyunsaturated C18 fatty acid is a linolenic acid (C18:3), and preferably an alpha-linolenic acid (alpha C18:3),
for a culture of *Leptospira* serogroup Canicola, the polyunsaturated C18 fatty acid is a linolenic acid (C18:3),
for a culture of *Leptospira* serogroup Pomona, the polyunsaturated C18 fatty acid is a gamma-linolenic acid (gamma C18:3), and/or
for a culture of *Leptospira* serogroup Sejroe (serovar Hardjo), the polyunsaturated C18 fatty acid is linoleic acid (C18:2), whereby the fatty acid can also be provided to the *Leptospira* culture in the form of a derivative, of that fatty acid, or in the form of a compound or composition relatively rich in the fatty acid, as defined herein.

In principle any polyunsaturated C18 fatty acid as defined above may be used in a method according to the invention, and provide generally the same effect. Even more so: the inventors have found that different types of polyunsaturated C18 fatty acid can also be provided to a culture in a combined supplementation, whereby their effects on the increase of antigenic mass were cumulative.

This is exemplified herein, for example for *Leptospira* from serogroup lcterohaemorrhagiae, where supplementation with the combination of 50 μg/ml of each of linoleic acid and of alpha-linolenic acid, produced an increase in antigenic mass that was very close to the arithmetic mean of the separate relative increases in antigenic mass from the supplementation of cultures (in the same experiment) with 100 μg/ml of either linoleic acid or alpha-linolenic acid.

The combined supplementation of polyunsaturated C18 fatty acids for the method according to the invention, can be by supplementing with a mixture of fatty acids (or of their derivatives, or compounds or compositions relatively rich in such fatty acids), or as separate supplementations, either simultaneous, consecutive, or more separated in time.

Therefore, in an embodiment, the polyunsaturated C18 fatty acid is supplemented to a *Leptospira* culture by using a composition that naturally contains more than one polyunsaturated C18 fatty acid. Examples are vegetable (seed) oils, e.g. Rapeseed or Flax seed oil, which are relatively rich in both C18:2 and alpha C18:3, or Hemp seed oil, which is relatively rich in C18:2, alpha C18:3, and gamma C18:3.

"*Leptospira*" refers generally to bacteria from the taxonomic genus of spirochete bacteria with that name. This includes also *Leptospira* that are sub-classified therefrom in any way, for instance as a subspecies, strain, isolate, genotype, serotype, serovar, serogroup, variant, or subtype and the like. Such *Leptospira* share the characterising features of their taxonomic family-members such as the genomic, physical, electron-microscopic, and biochemical characteristics, as well as biological characteristics such as physiologic, immunologic, or pathogenic behaviour. Next to serological classification, other determinations can be based on nucleotide sequencing or PCR assays, as known in the field.

It will be apparent to a skilled person that while the bacterial genus that is the subject of the present invention is currently named *Leptospira*, this is a taxonomic classification which could be subject to change as new insights lead to reclassification into a new or different taxonomic group. However, as this does not change the micro-organism involved or its characterising features, only its scientific name or classification, such re-classified organisms remain within the scope of the invention.

Preferred *Leptospira* for use in a method according to the invention are *Leptospira* that are pathogenic to one or more animal species or to humans; more preferred is at least one serogroup selected from *L. interrogans* (sensu lato) Canicola, Icterohaemorrhagiae, Australis, Grippotyphosa, Pomona, Tarassovi, Sejroe and Autumnalis.

Even more preferred is at least one serovar selected from *L. interrogans* (sensu lato) Canicola, Portland-vere, *Ictero-*

*haemorrhagiae*, Copenhageni, Bratislava, Australis, Grippotyphosa, Dadas, Pomona, Tarassovi, Gatuni, Hardjo, Saxkoebing and Autumnalis.

A "culture" for the invention is: a composition comprising *Leptospira* bacteria. The bacteria in a *Leptospira* culture for the invention can be in different densities or conditions: intact or not, alive or dead, (partially) ruptured or inactivated, etc. The bacteria can be in any cell-cycle phase such as proliferating, resting, or dormant. The culture can be a proliferating culture, where the *Leptospira* are recently inoculated, early-, mid-, late exponential- or log-phase. Or the culture can be a static or stationary culture, where the *Leptospira* are in lag phase, or in a harvested, or stored culture.

The composition comprising the *Leptospira* bacteria can be liquid, solid or semi-solid, frozen, or freeze-dried. The composition can be a culture medium, or a storage medium, and can comprise a stabiliser, or another pharmaceutically acceptable additive or carrier. Inter alia such a culture comprises a cell-suspension.

In a preferred embodiment, the culture for use in a method according to the invention is in liquid form, as this facilitates the uptake by the *Leptospira* of a polyunsaturated C18 fatty acid.

For the invention the term "comprising" (as well as variations such as "comprise", "comprises", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprising" (or its variations) is replaced by terms such as "consist of", "consisting of", or "consist essentially of".

For the invention "supplementing" has the common meaning of: adding to supply a deficiency, or to reinforce or extend something (from: American heritage dictionary, ed. Houghton Miflin Co., Boston, USA).

The way in which the supplementation of a polyunsaturated C18 fatty acid in a method according to the invention is applied, is in principle not limited, as long as the effect of said method can be reached: a relative increase of the antigenic mass. Thus, for a method according to the invention, supplementing a polyunsaturated C18 fatty acid can be done by addition to an existing culture of *Leptospira*, either once, repeatedly, or continuously. Alternatively, supplementing a culture of *Leptospira* in a method according to the invention, can be done by providing a certain concentration of a polyunsaturated C18 fatty acid at the moment of establishing the culture of *Leptospira* for the invention. For example by providing a certain concentration of a polyunsaturated C18 fatty acid in a culture medium in which a *Leptospira* culture is to be inoculated and proliferated, or in a washing-, storage-, or incubation medium in which a *Leptospira* culture is to be kept or treated.

Also, the supplementation with a polyunsaturated C18 fatty acid can be at different time points in the lifecycle of the *Leptospira*, such as in the early, mid, or late stage of an actively proliferating culture, or in a stored sample; and at different densities of the bacterial cells.

The polyunsaturated C18 fatty acid can be in different forms, and can be supplemented in different ways. Options for variation and optimisation of these conditions are described and exemplified herein, and are well within the routine capabilities of the skilled artisan.

In a preferred embodiment the supplementing for a method according to the invention is done by adding a polyunsaturated C18 fatty acid to a proliferating *Leptospira* culture, and by adding gradually over time.

For the invention "a polyunsaturated C18 fatty acid" refers to the chemical compound that is the fatty acid, or to a derivative thereof, but also to a polyunsaturated C18 fatty acid in a mixture or complex, or to a compound or composition that is relatively rich in a polyunsaturated C18 fatty acid. A compound or composition is "relatively rich" in a polyunsaturated C18 fatty acid, if it comprises a polyunsaturated C18 fatty acid in an amount of at least about 5% of its total amount of fatty acids. Preferably at least about 10, 15, 20, 25, 30, 40, 50% of its total amount of fatty acids, in that order of preference.

Determination of fatty acid content, as well as the differentiation into the relative amounts of individual fatty acids, can routinely be done by a skilled person, for example by extraction and gas-chromatography. Examples of compounds and compositions that are relatively rich in a polyunsaturated C18 fatty acid, for use in a method according to the invention, are described below.

The term "polyunsaturated C18 fatty acid" is used in its common meaning, relating to a fatty acid with a hydrocarbon chain containing 18 C atoms, and which hydrocarbon chain contains more than one double (unsaturated) bond.

Known in the art are conjugated polyunsaturated C18 fatty acids, which are produced (ergo not consumed) by bacteria such as Lactobacilli, in the rumen of ruminants.

In a preferred embodiment, the polyunsaturated C18 fatty acid for use in the invention is non-conjugated.

In a further preferred embodiment, the polyunsaturated C18 fatty acid for use in the invention is a methylene interrupted polyene, is not branched, and/or is not bound to a cyclo-alkane ring.

In an even further preferred embodiment, the polyunsaturated C18 fatty acid for use in the invention is an omega 3-or an omega 6 polyunsaturated C18 fatty acid.

In a still further preferred embodiment, the polyunsaturated C18 fatty acid for use in the invention is one or more selected from the group consisting of C18:2, C18:3, and C18:4.

In the most preferred embodiment, the polyunsaturated C18 fatty acid for use in the invention is one or more selected from the group consisting of: linoleic acid, alpha-linolenic acid, gamma-linolenic acid, or stearidonic acid.

"Linoleic acid" is a C18:2, n-6, delta 9,12 fatty acid, with scientific name: 9, 12-octadecadienoic acid, and CAS nr.: 60-33-3. Preferably both its double bonds are in the cis form.

Linolenic acid is a C18:3 fatty acid, with two isomeric forms: alpha-linolenic acid, and gamma-linolenic acid.

"Alpha-linolenic acid" is a C18:3, n-3, delta 9, 12, 15 fatty acid, with scientific name: 9, 12, 15-octadecatrienoic acid, and CAS nr.: 463-40-1. Preferably all its double bonds are in the cis form.

"Gamma-linolenic acid" is a C18:3, n-6, delta 6, 9, 12 fatty acid, with scientific name: 6, 9, 12-octadecatrienoic acid, and CAS nr.: 506-26-3. Preferably all its double bonds are in the cis form.

"Stearidonic acid" is a C18:4, n-3, delta 6, 9, 12, 15 fatty acid, with scientific name: 6, 9, 12, 15-octadecatetraenoic acid, and CAS nr. 20290-75-9. Stearidonic acid is also known as moroctic acid. Preferably all its double bonds are in the cis form.

The polyunsaturated C18 fatty acid may be of natural or of synthetic origin, and may be in isolated state or in any degree of purity. Also the polyunsaturated C18 fatty acid may be bound, coupled or esterified to other chemical groups. All these forms are allowable as long as the polyunsaturated C18 fatty acid is biologically available to the *Leptospira* culture, and the effect of a method according to the invention can be obtained. Preferably the polyunsaturated C18 fatty acid is in a form that is not too toxic for the *Leptospira* culture, and that can be used in the context of aqueous culture conditions.

A skilled person can readily determine if a polyunsaturated C18 fatty acid, a derivative, or a compound or composition containing a polyunsaturated C18 fatty acid, can be used in a method according to the invention, or is too toxic or inconvenient, by the details and examples provided herein.

For example by testing such a fatty acid, derivative, compound or composition in a representative small scale fermentation of *Leptospira*, and determining the amount of *Leptospira* LPS antigen of a certain number of cells, and compare that to the antigen amount of cells from a similar *Leptospira* culture which was not supplemented with the a polyunsaturated C18 fatty acid containing compound or composition.

Examples of polyunsaturated C18 fatty acids, derivatives, compounds and compositions for use in the invention are: a polyunsaturated C18 fatty acid as available in a variety of purities from all major suppliers of bio-chemicals. Also the polyunsaturated C18 fatty acid can be bound on or complexed to a carrier molecule, such as a protein or protein complex (e.g. serum or albumin, an enzyme (acyl-CoA), or esterified to a glycerol or cholesterol, or as a lipoprotein, a phospholipid (bound to a phosphate), or a glycolipid or lipopolysaccharide (bound to a carbohydrate moiety). Also the polyunsaturated C18 fatty acid can be present as a minor free acid component in a composition of other fatty acids. Alternative the polyunsaturated C18 fatty acid may be present in a compound or composition relatively rich in polyunsaturated C18 fatty acid, such as a vegetable (seed) oil.

As a fatty acid is normally poorly soluble in an aqueous medium, the polyunsaturated C18 fatty acid, or a derivative, or a compound or composition relatively rich in a polyunsaturated C18 fatty acid, can be made into a preparation that facilitates its supplementation to a *Leptospira* culture, so as to make or keep it bioavailable. For example the polyunsaturated C18 fatty acid may be physically dispersed, or chemically emulsified, or mixed with a solvent. It can be combined with a carrier such as a cellulose, cyclodextrin, or cholesterol, or by using BSA or serum as described above; alternatively a polyunsaturated C18 fatty acid can be transferred via a particulate adsorbent such as e.g. Celite® or Amberlite® (Spector & Hoak, supra).

An advantageous way to supplement a culture of *Leptospira* with a polyunsaturated C18 fatty acid in a method according to the invention, is by supplementing the culture with BSA that was created to comprise a high amount of a polyunsaturated C18 fatty acid.

Therefore in a preferred embodiment of a method according to the invention, the polyunsaturated C18 fatty acid is supplemented in the form of a complex to BSA.

A polyunsaturated C18 fatty acid can be loaded onto BSA by simple co-incubation, until the BSA is saturated with the polyunsaturated C18 fatty acid. Binding of fatty acid to BSA is temperature and pH dependent, as is known in the art, and described e.g. in: Spector & Hoak (supra), and Ashbrook et al. (1975, J. of Biol. Chem., vol. 250, p. 2333). The load level of a polyunsaturated C18 fatty acid on the BSA can conveniently be analysed by gas-chromatography as described below. How much of a polyunsaturated C18 fatty acid can be taken up by the BSA, depends on the type and the quality of the BSA, as well as on the amount of fatty acid that was already bound. If maximal loading of a polyunsaturated C18 fatty acid is desired, BSA can first be delipidated by extraction, and then reloaded exclusively with a polyunsaturated C18 fatty acid. A BSA that was loaded with (additional) polyunsaturated C18 fatty acid can be used in *Leptospira* cultures, instead of, or in addition to, the BSA or serum that is already used in the culture medium.

The inventors have found that effective supplementation for a method according to the invention was possible using a BSA that was created to contain at least about 10% w/w of its fatty acids as a polyunsaturated C18 fatty acid.

Therefore a preferred composition for supplementing a polyunsaturated C18 fatty acid for a method according to the invention, is a BSA preparation comprising at least about 10% w/w of its free fatty acid as a polyunsaturated C18 fatty acid; preferably comprising at least 12, 15, 18, 20, 21, 23, 25, 30, 35, 40, 50, 60, 70, 75, 80, 90, 95, or 99% w/w of its free fatty acid as a polyunsaturated C18 fatty acid, in this order of preference.

The skilled person will appreciate that when a *Leptospira* culture is supplemented with a poly-unsaturated C18 fatty acid according to the method of the invention, using a BSA preparation, this may increase the protein load of the culture, and thus of the vaccine produced therefrom. This could have an effect on the level of vaccination side effects. Such a culture may therefore require a purification step to get rid of excess proteins. However, as such purification is often being applied anyway, therefore the supplementation of a polyunsaturated C18 fatty acid in a complex with BSA or serum is a highly effective way to increase the antigenic mass of a *Leptospira* culture.

The polyunsaturated C18 fatty acid (-preparation) can be supplemented to a *Leptospira* culture according to the method of the invention, in different ways, e.g. as a pulse, or more gradually over time. A pulse supplementation e.g. would be to supplement all the polyunsaturated C18 fatty acid within about 1 hour, and this would be most appropriate in case the culture is static. For proliferating *Leptospira* cultures, most appropriate supplementations are a gradual supplementation, which would mean to add all polyunsaturated C18 fatty acid in a time period of between about 1 to about 6 hours. A fed-batch supplementation for a proliferating culture, would mean to have a feed of a polyunsaturated C18 fatty acid(-preparation) going for most of the culture duration.

In a preferred embodiment of a method according to the invention, a proliferating culture of *Leptospira* is supplemented gradually or in fed-batch mode.

The amount of a polyunsaturated C18 fatty acid that is to be supplemented to a *Leptospira* culture to achieve a relative increase in antigenic mass, as in a method according to invention, is in principle only limited by what is feasible from practical, economical, and biological perspective. For example practical considerations are that a fermenter vessel with a proliferating culture should not be opened multiple times for adding a supplement, as that may compromise a safe operation and its sterility. On the other hand when the culture that is to be supplemented is not actively proliferating, such as an end culture, or a stored culture, there is much less risk of a contamination over-proliferating the culture. Economic considerations are for example the material costs of supplementing a large amount of a pure polyunsaturated C18 fatty acid, or a special polyunsaturated C18 fatty acid-combination product.

Biological considerations are that free fatty acids can be toxic to live cells, although that is less of an issue for a static culture. Therefore, when large amounts of a polyunsaturated C18 fatty acid are to be supplemented to a proliferating culture in a short period of time, care must be taken to mitigate or prevent toxicity of the fatty acid to the *Leptospira*, for example by providing the polyunsaturated C18 fatty acid in a complex to reduce toxicity, as described above. Alternatively the polyunsaturated C18 fatty acid can be supplemented gradually over time.

Further parameters to consider are the conditions of each specific case: the amount, status, and type of the *Leptospira*, as well as the incubation medium, temperature, pH, etc. With the details and examples herein, it is within the reach of a skilled person to vary and optimise the amount and the way in which a polyunsaturated C18 fatty acid is supplemented to a *Leptospira* culture in the context of a method according to the invention.

The *Leptospira* in a culture seem to consume a polyunsaturated C18 fatty acid as soon as they can. See for example FIGS. 2, 3 and 13, 14 which illustrate that linoleic acid and linolenic acid are very rapidly consumed and converted into antigenic mass, in contrast to palmitic acid and oleic acid. This means that the total amount of antigenic mass generated in such a culture is a result of the cumulative total amount of polyunsaturated C18 fatty acid that was available to the culture during incubation. For the invention, the indication of the amount of a polyunsaturated C18 fatty acid that is supplemented to a culture therefore refers to the total amount of a polyunsaturated C18 fatty acid that was made available during the proliferating or incubation of a *Leptospira* culture, as if all the polyunsaturated C18 fatty acid was available at a single time point. It is expressed as a concentration based on the total volume of the culture. This is independent of the form or volume of the mixture that the polyunsaturated C18 fatty acid was comprised in, and includes additions made by all media components.

Consequently, a skilled person will appreciate that it will often not be possible to actually measure this total concentration of polyunsaturated C18 fatty acid provided to the *Leptospira* culture. On the one hand because it is a cumulative number from polyunsaturated C18 fatty acid contributions made over time and from different components. On the other hand because the *Leptospira* culture will already have taken up and processed part of it before the moment of sampling.

For example, the inventors demonstrated that a significant increase of the antigenic mass could be obtained when supplementing a culture of *Leptospira* according to the method of the invention with linoleic acid, such that 25 µg linoleic acid had been made available per ml of culture, as compared to a culture which had available only about 5 µg/ml.

The same applies for linolenic acid, although standard EMJH culture medium contains negligible amounts of C18: 3. Consequently, in principle the supplementation of any amount of C18:3 to a *Leptospira* culture, will already be beneficial to its antigenic mass/biomass ratio. In practice amounts of a C18:3 can be added starting from about 5 µg/ml.

At higher amounts of available polyunsaturated C18 fatty acid, antigenic masses further increased. At the highest availability level tested, above 300 µg/ml of a polyunsaturated C18 fatty acid in a *Leptospira* culture, some toxicity was noticeable for some serovars. However this effect was seen when using a preparation of pure polyunsaturated C18 fatty acid for the supplementation, and can be overcome by appropriate detoxification of the polyunsaturated C18 fatty acid in a complex, as described above.

Therefore in an embodiment, the invention provides a method for increasing the antigenic mass of a *Leptospira* culture, the method comprising the step of incubating said *Leptospira* culture under conditions in which at least 15 µg/ml linoleic acid, and/or at least 5 µg/ml of a linolenic acid was made available to said culture.

As described below, the supplementation of different polyunsaturated C18 fatty acids-as defined above-can also be combined, giving a cumulative effect in a *Leptospira* culture. Consequently, the total amount of polyunsaturated C18 fatty acids that is made available to a *Leptospira* culture, can thus be based on the sum of the amounts of the different polyunsaturated C18 fatty acids that are combined.

Therefore, in a preferred embodiment of a method according to the invention, the method comprises the step of incubating a *Leptospira* culture under conditions in which at least 15 µg polyunsaturated C18 fatty acid/nnlwas made available to said culture. More preferably at least 16, 17, 18, 19, 20, 21, 22, 23, 24, 25, 26, 27, 28, 29, 30, 32, 35, 37, 40, 45, 50, 55, 60, 65, 70, 75, 80, 85, 90, 95, or at least 100 µg polyunsaturated C18 fatty acid/ml was made available to said culture, in that order of preference.

In a further preferred embodiment of a method according to the invention, the method comprises the step of incubating a *Leptospira* culture under conditions in which between about 15 and 1000 µg polyunsaturated C18 fatty acid/mi was made available to said culture. More preferably between about 20 and 500 µg/ml, between about 20 and 300 µg/ml, or between about 25 and 250 µg polyunsaturated C18 fatty acid/ml was made available to said culture, in that order of preference.

In an embodiment the invention provides a method for increasing the antigenic mass of a *Leptospira* culture, the method comprising the step of supplementing said *Leptospira* culture with a polyunsaturated C18 fatty acid under conditions in which at least 15 µg of a polyunsaturated C18 fatty acid/ml was made available to said culture; wherein the *Leptospira* is at least one serogroup selected from *L. interrogans* (sensu lato) Canicola, Icterohaemorrhagiae, Australis, Grippotyphosa, Pomona, Tarassovi, Sejroe and Autumnalis; and wherein the increase of the antigenic mass of said *Leptospira* culture is with at least 20%, as compared to the antigenic mass of a similar *Leptospira* culture that was not supplemented with a polyunsaturated C18 fatty acid.

In a further aspect the invention provides a *Leptospira* culture obtainable by a method according to the invention, wherein said *Leptospira* culture has an increased antigenic mass.

Such a *Leptospira* culture according to the invention differs from a *Leptospira* culture of the prior art, in that the *Leptospira* culture has an antigenic mass that is significantly increased resulting from supplementation with a polyunsaturated C18 fatty acid as in a method according to the invention. The increased antigenic mass is readily detectable and quantifiable as described: an increase in antigenic mass by 20% or more is significant and detectable, as described above.

The increase in antigenic mass is relative to the antigenic mass of a similar *Leptospira* culture under similar condition, but which has not been supplemented with a polyunsaturated C18 fatty acid as in a method according to the invention, as described above.

Therefore a *Leptospira* culture according to the invention is characterised in that the antigenic mass of said *Leptospira* culture is increased with at least 20% as compared to the antigenic mass of a similar *Leptospira* culture that was not supplemented with a polyunsaturated C18 fatty acid.

More preferably a *Leptospira* culture according to the invention is characterised in that the antigenic mass of said *Leptospira* culture is increased with at least 22, 24, 25, 28, 30, 35, 40, 45, 50, 63, 77, 90, 100, 121, 150, 175, 184, or with at least 200%, in that order of preference, and as compared to the antigenic mass of a similar *Leptospira* culture that was not supplemented with a polyunsaturated C18 fatty acid.

A *Leptospira* culture according to the invention is obtainable by a method according to the invention as described, for example by supplementing *Leptospira* in a proliferating-, or stationary culture, or a culture harvest, with a polyunsaturated C18 fatty acid, a derivative, or a compound or composition that is relatively rich in a polyunsaturated C18 fatty acid. This has several advantageous utilities, amongst which in vaccines against *Leptospirosis*.

In a further aspect the invention relates to a *Leptospira* culture according to the invention, or a preparation of said culture, for use in a vaccine against Leptospirosis.

Preferably a *Leptospira* culture for use in a vaccine against Leptospirosis according to the invention is in the form of an inactivated *Leptospira* culture according to the invention.

For the invention, "a preparation" of a *Leptospira* culture according to the invention, may be a fragment of such a culture, for example an extract, sonicate, or filtrate, or a subunit from a *Leptospira* culture according to the invention, such as a part of the outer envelope containing LPS, a purified LPS, or a part of said LPS.

Therefore, in a further aspect the invention provides a vaccine against Leptospirosis comprising a *Leptospira* culture according to the invention, or a preparation of said culture.

A "vaccine" for the invention is a pharmaceutical composition comprising an immunologically effective amount of (a preparation of) a *Leptospira* culture according to the invention, and a pharmaceutically acceptable carrier. The vaccine induces an effective immune-response against Leptospirosis.

A "pharmaceutically acceptable carrier" is intended to aid in the effective administration of a pharmaceutically active compound, without causing (severe) adverse effects to the health of the target to which it is administered. A pharmaceutically acceptable carrier can for instance be sterile water or a sterile physiological salt solution. In a more complex form the carrier can e.g. be a buffer, which can comprise further additives, such as stabilisers or preservatives.

The Leptospiral component of a vaccine against Leptospirosis according to the invention, will induce in the target human or animal an immune response that will assist to prevent, ameliorate, or reduce an infection with *Leptospira*, or of the intensity of clinical signs of Leptospirosis, as caused by infecting *eptospira*. This may be the result of a reduced colonization or of a reduced infection rate by the *Leptospira*, leading to a reduction in the number or the severity of lesions and effects that are caused by the *Leptospira*, or by the target's response thereto. In addition, this will reduce the (urinary) excretion of *Leptospira*, and thereby the spread into the environment, which reduces the chance of zoonotic infections.

What constitutes an immunologically effective amount of a vaccine against Leptospirosis according to the invention is dependent on the desired effect and on the specific characteristics of the vaccine that is being used, and the target to which it is to be applied. For bacterin-based Leptospirosis vaccines, which function essentially by a humoral immune response, the correlation is well known between a certain antigenic mass, and the immunoprotective strength of the vaccine in a target. Therefore the determination of an effective amount is well within the skills of the routine practitioner, for instance by monitoring the immunological response following vaccination, or after a challenge infection, e.g. by monitoring the targets' clinical signs of disease, serological parameters, or by re-isolation of the pathogen, and comparing these to responses seen in unvaccinated animals.

In a preferred embodiment the vaccine according to the invention additionally comprises a stabiliser, e.g. to protect degradation-prone components, and/or to enhance the shelf-life of the vaccine. Generally such stabilisers are large molecules of high molecular weight, such as lipids, carbohydrates, or proteins; for instance milk-powder, gelatine, serum albumin, sorbitol, trehalose, spermidine, Dextrane or polyvinyl pyrrolidone, and buffers, such as alkali metal phosphates.

Preferably the stabiliser is free of compounds of animal origin, or even: chemically defined, as disclosed in WO 2006/094,974.

Also preservatives may be added, such as thimerosal, phenolic compounds, and/or gentamicin.

General techniques and procedures in vaccinology are well known in the art and are described for instance in governmental regulations such as the Pharmacopeia, and in well-known handbooks such as: "Veterinary vaccinology" (P. Pastoret et al. ed., 1997, Elsevier, Amsterdam, ISBN: 0444819681), and: "Remington: the science and practice of pharmacy" (2000, Lippincot, USA, ISBN: 683306472).

Target subjects for a vaccine according to the invention can be humans or a wide variety of animals that are susceptible to infection with *Leptospira*. Preferred targets are one or more selected from: human, canine, porcine, bovine, equine, caprine, ovine and cervine. In principle the target may be healthy or diseased, and may be positive or-negative for presence of *Leptospira*, or for antibodies against *Leptospira*. Also the target can be of any age at which it is susceptible to the vaccination. However it is evidently favourable to vaccinate healthy, uninfected targets, and to vaccinate as early as possible to prevent any field infection.

A vaccine according to the invention can serve as an effective priming vaccination, which can later be followed and amplified by a booster vaccination.

A vaccine according to the invention can equally be used as prophylactic-and as therapeutic treatment, as it interferes both with the establishment and with the progression of a *Leptospira* infection or its clinical signs of disease.

The scheme of the application of a vaccine according to the invention to the target can be in single or multiple doses, which may be given at the same time or sequentially, in a manner compatible with the dosage and formulation, and in such an amount as will be immunologically effective.

The protocol for the administration of a vaccine according to the invention ideally is integrated into existing vaccination schedules of other vaccines that the target may require.

The vaccine according to the invention is preferably applied as a single yearly dose.

A vaccine according to the invention can contain an amount of *Leptospira* from a culture according to the invention, or of the preparation thereof, corresponding to between 1×10^6 and 1×10^10 bacterial cells per dose; preferably between 1×10^7 and 5×10^9 per dose.

Vaccines according to the invention, can be administered in a volume that is consistent with the target, and can for instance be between about 0.1 and 10 ml in volume. Preferably one dose is between about 0.25 and 3 ml.

A vaccine according to the invention can be administered to a target according to methods known in the art. For instance as a parenteral application by any route of injection into or through the skin: e.g. intramuscular, intravenous, intraperitoneal, intradermal, submucosal, or subcutaneous. Alternative routes of application that are feasible are by topical application, by inhalation, or via the alimentary route.

The preferred application route is by intramuscular or by subcutaneous injection. It goes without saying that the optimal route of application will depend on the specific vaccine formulation that is used, and on the particular characteristics of the target.

It is well within reach of a skilled person to further optimise a vaccine according to the invention. Generally this involves the fine-tuning of the efficacy of the vaccine, so that it provides sufficient immune-protection. This can be done by adapting the vaccine dose, or by using the vaccine in another form or formulation, or by adapting the other constituents of the vaccine (e.g. the stabiliser or the adjuvant), or by application via a different route.

The vaccine may additionally comprise other compounds, such as an adjuvant, an additional antigen, a cytokine, etc. Alternatively, a vaccine according to the invention can advantageously be combined with a pharmaceutical component for example an antibiotic, a hormone, or an anti-inflammatory drug.

In a preferred embodiment, a vaccine according to the invention is characterised in that it comprises an adjuvant.

An "adjuvant" is a well-known vaccine ingredient, which in general is a substance that stimulates the immune response of the target in a non-specific manner. Many different adjuvants are known in the art. Examples of adjuvants are Freund's Complete and-Incomplete adjuvant, vitamin E, aluminium compositions, non-ionic block polymers and polyamines such as dextransulphate, Carbopol® and pyran.

Furthermore, peptides such as muramyldipeptides, dimethylglycine, tuftsin, are often used as adjuvant, and mineral oil e.g. Bayol™ or Markol™, Montanide™ or light paraffin oil, vegetable oils or combination products such as ISA™ from Seppic™, or DiluvacForte™ can advantageously be used. An emulsion can be water-in oil (w/o), oil-in water (o/w), water-in-oil-in-water (w/o/w), double oil-emulsion (DOE), etc.

Preferred adjuvants for a vaccine according to the invention are aluminiumhydroxide, or Saponin, such as : Quil A®, or Q-vac®. Saponin and vaccine components may be combined in an ISCOM® (EP 109.942, EP 180.564, EP 242.380).

It goes without saying that other ways of adjuvating, adding vehicle compounds or diluents, emulsifying or stabilizing a vaccine are also within the scope of the invention.

A vaccine according to the invention can advantageously be combined with another antigen into a combination vaccine.

Therefore, in a more preferred embodiment a vaccine according to the invention is characterised in that it comprises an additional immunoactive component.

An "additional immunoactive component" may be an antigen, an immune enhancing substance, and/or a vaccine, either of which may comprise an adjuvant. The additional immunoactive component when in the form of an antigen may consist of any antigenic component of human or veterinary importance. Preferably the additional immunoactive component is based upon, or derived from, a further micro-organism that is pathogenic to the target. It may for instance comprise a biological or synthetic molecule such as a protein, a carbohydrate, a lipopolysaccharide, a nucleic acid encoding a proteinaceous antigen. Also a host cell comprising such a nucleic acid, or a live recombinant carrier micro-organism containing such a nucleic acid, may be a way to deliver the nucleic acid or the additional immunoactive component. Alternatively it may comprise a fractionated or killed micro-organism such as a parasite, bacterium or virus.

The additional immunoactive component(s) may also be an immune enhancing substance e.g. a chemokine, or an immunostimulatory nucleic acid, e.g. a CpG motif. Alternatively, the vaccine according to the invention, may itself be added to a vaccine.

An advantageous utility of a combination vaccine for the invention is that it not only induces an immune response against *Leptospira*, but also against other pathogens of a target, while only a single handling of the target for the vaccination is required, thereby reducing discomfort to the target, as well as time- and labour costs.

Examples of such additional immunoactive components are in principle all viral, bacterial, and parasitic pathogens amenable to vaccination of a target that is also a target for a vaccine against Leptospirosis according to the invention.

For example, for porcines: porcine circovirus, porcine reproductive and respiratory syndrome virus, pseudorabies virus, porcine parvo virus, classical swine fever virus, *Mycoplasma hyopneumoniae, Lawsonia intracellularis, E. coli, Streptococcus* spec., *Salmonella* spec., *Clostridia* spec., *Actinobacillus pleuropneumoniae, Pasteurella* spec., *Haemophilus* spec., *Erysipelothrix* spec., *Bordetella* spec., etc.

For bovines: *Neospora* spec., *Dictyocaulus* spec., *Cryptosporidium* spec., *Ostertagia* spec., bovine rotavirus, bovine viral diarrhoea virus, bovine coronavirus, bovine infectious rhinotracheitis virus (bovine herpes virus), bovine paramyxovirus, bovine parainfluenza virus, bovine respiratory syncytial virus, rabies virus, bluetongue virus, *Pasteurella haemolytica, E. coli, Salmonella* spec., *Staphylococcus* spec., *Mycobacterium* spec., *Brucella* spec., *Clostridia* spec., *Mannheimia* spec., *Haemophilus* spec., *Fusobacterium* spec., etc.

For ovines or caprines: *Toxoplasma gondii*, peste des petit ruminant virus, bluetongue virus, Schmallenberg virus, *Mycobacterium* spec., *Brucella* spec., *Clostridia* spec., *Coxiella* spec., *E. coli, Chlamydia* spec., *Clostridia* spec., *Pasteurella* spec., *Mannheimia* spec., etc.

For canines or felines: *Ehrlichia canis, Leishmania donovani*-complex, Neospora caninum, canine parvovirus, canine distemper virus, canine adenovirus types 1 or 2, canine hepatitis virus, canine coronavirus, canine parainfluenza virus, rabies virus, feline calicivirus, feline herpesvirus, feline panleucopenia virus, *Clostridium* spec., *Hepatozoon* spec., *Borrelia burgdorferi, Bordetella bronchiseptica, Chlamydia* spec., and species of *Babesia* or *Theileria*.

For humans: *Plasmodium, Leishmania, Toxoplasma*, varicella zoster virus, HIV, human papillomavirus, measles virus, mumps virus, rubella virus, rabies virus, poliovirus, rotavirus, respiratory syncytial virus, hepatitis virus spec., influenza virus, *Haemophilus* spec., *Streptococcus* spec., *Corynebacterium* spec., *Bordetella* spec., *Neisseria* spec., and *Clostridium* spec.

In an alternate embodiment, a combination vaccine for the invention can advantageously combine *Leptospira* from more than one serogroup of *L. interrogans*, For example, for a canine target: *L. interrogans* (sensu lato) serogroups Canicola and Icterohaemorrhagiae; or: *L. interrogans* (sensu lato) serogroups Canicola, Icterohaemorrhagiae, Australis, and Grippotyphosa. From these, one or more may be (derived from) a *Leptospira* culture according to the invention; preferably all are (derived from) *Leptospira* cultures according to the invention.

In a further preferred embodiment of a combination vaccine for the invention, the combination vaccine comprises (next to an additional immunoactive component), one or more *Leptospira* that correspond to more than one serogroups of *L. interrogans*. For example for a porcine target the combination vaccine may comprise: *L. interrogans* (sensu lato) serogroups Canicola, Icterohaemorrhagiae, Australis, Grippotyphosa, Pomona and Tarassovi, as well as *Erysipelothrix rhusiopathiae* and porcine parvovirus.

In this combination, one or more of the *Leptospira* may be a *Leptospira* culture according to the invention; preferably all are *Leptospira* cultures according to the invention.

For practical, and process control reasons, it is beneficial to produce each of the *Leptospira* antigens in such a combination vaccine in separate cultures according to the invention. This because each can then be produced with its specific optimal conditions. Next separate vaccine antigens will be prepared, and only then the different *Leptospira* antigens will be combined.

In a further aspect the invention relates to the use of a *Leptospira* culture according to the invention, or of a preparation of said *Leptospira* culture, for the manufacture of a vaccine against Leptospirosis.

The "manufacture" of a vaccine for the invention is carried out by means well known to the skilled person. Such manufacture will in general comprise the steps of admixing and formulation of a *Leptospira* culture according to the invention, or of a preparation thereof, with pharmaceutically acceptable excipients, followed by apportionment into appropriate sized containers. The various stages of the manufacturing process will need to be monitored by adequate tests, for instance by immunological tests for the quality and quantity of the antigens; by micro-biological tests for sterility and absence of extraneous agents; and ultimately by in vitro or in vivo experiments to determine vaccine efficacy and—safety. All these are well known to a skilled person.

A vaccine according to the invention can be manufactured into a form that is suitable for administration to human or animal targets, and that matches with the desired route of application, and with the desired effect.

Well known forms of vaccines are e.g.: a liquid, a gel, an ointment, a powder, a tablet, or a capsule, depending on the desired method of application to the target. Preferably a vaccine according to the invention is formulated as an injectable liquid, such as: a suspension, solution, dispersion, or emulsion. Commonly such vaccines are prepared sterile.

In one embodiment a vaccine according to the invention is based on a *Leptospira* culture according to the invention that was inactivated. Such a bacterin based inactivated vaccine can now be manufactured for the invention using well known techniques.

Therefore, in a further aspect the invention provides a method for producing a vaccine against Leptospirosis, said method comprising the steps of:
  a. proliferating a *Leptospira* culture in an in vitro system,
  b. supplementing said *Leptospira* culture with a polyunsaturated C18 fatty acid,
  c. inactivating and harvesting said supplemented *Leptospira* culture, and
  d. admixing the inactivated *Leptospira* culture with a pharmaceutically acceptable carrier.

The method is performed according to well-known procedures for the proliferation, inactivation and formulation of Leptospirosis vaccines. The harvesting is also performed as in the prior art, except that there are now more options to choose the time point for the harvest than in the prior art: when a prior art level of antigenic mass is required, the harvest can now be made earlier than previously.

Alternatively, when a maximal antigenic mass is desired, the culture can first be allowed to proliferate to its maximal biomass, as was done previously, only that now significantly more antigen amount is produced when the culture is supplemented with a polyunsaturated C18 fatty acid as in a method according to the invention.

The term "proliferating" has the common meaning of enabling and inducing the *Leptospira* bacteria to go through a number of cycles of cell division. Proliferating for the invention incorporates the meaning of similar terms indicating an increase in cell-numbers and cell-size, such as 'growing', 'culturing', or 'amplifying'. The proliferation phase is preceded by inoculation, and this in turn may be preceded by strain selection, pre-conditioning, and/or and pre-proliferation.

An "in vitro system" is a well-known way of deliberate proliferation of *Leptospira* bacteria outside of a human or animal organism, under controlled artificial conditions. This typically employs a chemostat or fermenter, and a (semi-) defined culture medium. Routinely, several critical parameters of the fermentation will be monitored and adjusted when appropriate, and this can even be automated. Techniques, materials and equipment for an in vitro bacterial cell proliferation system at any scale is well known and readily available from many commercial suppliers to the life-science industry.

In a preferred embodiment of a method for producing a vaccine according to the invention, an intervening step is introduced, which allows the process to be run non-continuously. The intervening step is introduced between the proliferating and the supplementing steps, and relates to a harvest, storage and/or purification of the *Leptospira* culture that was proliferated in the first step.

Therefore, in a preferred embodiment, a method for producing a vaccine against Leptospirosis according to the invention comprises between the first and the second step, an additional step comprising harvesting, storage and/or purification, of a *Leptospira* culture.

This intervening step allows for the separate performance and optimization of the proliferating-and the supplementing phases of a method according to the invention. The intervening step is performed in a way that maintains the viability or the biochemical integrity of the *Leptospira* culture, in way that allows its effective use in the further steps of the method. For example, the harvesting can be done e.g. by centrifugation or dia-filtration. As a result of the harvesting, the *Leptospira* can be in a more concentrated form. The storage can be performed at a temperature between about 2 and about 30° C. in an aqueous environment. The purification can comprise a refreshment or a replacement of the proliferation medium, for example to provide optimal conditions for the subsequent steps. Each of these manipulations can be performed separate, combined, or subsequently, and in any logical order.

In a method according to the invention, a *Leptospira* culture is supplemented with a polyunsaturated C18 fatty acid. However, a polyunsaturated C18 fatty acid as an ultrapure chemical may be too expensive for large scale use in the production of a low margin product such as applies to some veterinary vaccines. Therefore the polyunsaturated C18 fatty acid for use in these methods can be supplemented in different forms or purities, such as in a derivative or a compound or composition that is relatively rich in a polyunsaturated C18 fatty acid, as was defined above.

Therefore, in a further aspect the invention relates to the use of a compound or composition that is relatively rich in a polyunsaturated C18 fatty acid for a method according to the invention.

The skilled person is more than capable to test and select compounds and compositions that are relatively rich in a polyunsaturated C18 fatty acid, and optimize their use in a method according to the invention.

A very economical source of a polyunsaturated C18 fatty acid for use in a method according to the invention is a vegetable oil, because some of these oils are well known to contain very high levels of a polyunsaturated C18 fatty acid, they are economically priced, and are available in a quality and purity that is acceptable for use in methods according to the invention.

Therefore in a preferred embodiment of a use according to the invention, the compound or composition that is relatively rich in a polyunsaturated C18 fatty acid is a vegetable oil.

A "vegetable oil" is an oil that is derived from a part of a plant, most often from the fruits and seeds, such as: berries, peas, beans, grains and nuts; alternatively from: leaf, stem, flower, flower bud, root, or beet. The vegetable oil can be isolated from its vegetable source material by pressing, extracting, etc.; methods to obtain and purify vegetable oils have been known from ancient times.

Examples of vegetable oils that are relatively rich in linoleic acid are listed in Table 1. The values given are in % w/w of total fatty acid content, and are approximate averages, which may vary and depend on the plant-variety and on the extraction process used. Reference: U.S. Department of Agriculture, National Nutrient Database for Standard Reference, release 24, September 2011.

TABLE 1

| Approximate content (in % w/w of total fatty acid) of linoleic acid in vegetable oils | |
|---|---|
| Safflower oil (1)(2) | 78% |
| Grape seed oil | 73% |
| Poppy seed oil | 70% |
| Sunflower oil (1)(2) | 68% |
| Hemp oil (1) | 60% |
| Corn oil | 59% |
| Wheatgerm oil | 55% |
| Cottonseed oil | 54% |
| Soybean oil | 51% |
| Walnut oil | 51% |
| Sesame oil | 45% |
| Rice bran oil | 39% |
| Pistachio oil | 33% |
| Peanut oil | 32% |
| Almond oil | 23% |

TABLE 1-continued

| Approximate content (in % w/w of total fatty acid) of linoleic acid in vegetable oils | |
|---|---|
| Rapeseed oil (3) | 21% |
| Linseed oil (4) | 15% |
| Olive oil | 10% |

(1) In these trivial names of the oils the seed is not specified, even though the oil is obtained from the seed.
(2) This does not regard the variant of this oil that is high in oleic acid.
(3) A variant of rapeseed oil is Canola ® oil, which has a reduced content of erucic acid.
(4) Linseed is also known as: flax seed.

Also, some more exotic non-food vegetable (seed) oils are relatively rich in linoleic acid; e.g. oils from the seeds of: Firethorn: 70% w/w of total fatty acids; Oregon grape: 52%; and Sarsaparilla: 51%, (S. Ozgül-Yücel 2005, J.A.O.C.S, vol. 82, p. 893).

Well known sources of alpha linolenic acid are seed oils from: Chia sage, Kiwi fruit, Perilla, Flax, Hemp, Lingonberry, Niger, Rubber, Camelina, Purslane, Sea buckthorne, and Rapeseed.

Well known sources of gamma linolenic acid are seed oils from: Evening primrose, Borage, Blackcurrant, Safflower, and Hemp.

Well known sources of stearidonic acid are seed oils from: Hemp, Blackcurrant, Corn gromwell, and Echium.

Therefore, for the invention, a vegetable oil having at least 25% w/w of total fatty acids as a polyunsaturated C18 fatty acid is preferred, more preferably a vegetable oil having at least 30, 40, 50, 60, 70, or even at least 75% w/w of total fatty acids as a polyunsaturated C18 fatty acid, in that order of preference.

A *Leptospira* culture according to the invention can advantageously also be used in diagnostic methods. Examples are the use in a diagnostic test for detection of *Leptospira* specific antibody or-antigen in a test-sample. For example, a preparation from a *Leptospira* culture according to the invention can be coated on a plate or carrier, or can be used as capture antigen. Alternatively, the preparation can be used as standard reference antigen with a high antigenic mass.

The invention will now be further described with reference to the following, non-limiting, examples.

EXAMPLES

1. General materials and methods
1.1. Proliferation of *Leptospira*
1.1.1 Bacterial Strains, Medium and Pre-proliferation
A working seed of a strain of *L. interrogans* was inoculated into EMJH medium and incubated at 29° C. for 3 to 5 days. If needed up to 5 consecutive pre-culture passages could be made, whereby the pre-cultures were visually inspected for sufficient proliferation (turbidity) as criterion for transfer to the next passage.

NB: Appropriate biosecurity and containment measures must be applied when working with live *Leptospira*.

1.1.2 Main Fermentation
All experiments were performed in 0.5, 2 or 20 L working volume, computer-controlled fermenters (Sartorius), which were filled with 0.5, 1 or 10 L sterile-filtered EMJH medium, respectively. The standard EMJH medium contained 1% w/v BSA and 0.125% w/v polysorbate 80. The pH of the medium was 7.4 ±0.1 at start. The fermenter was inoculated with 5% v/v serogroup Icterohaemorrhagiae pre-culture (passage 5), giving an inoculation density of $2-4 \times 10^7$ cells/ml at day 0. End yields of *Leptospira* biomass were typically about $1-2 \times 10^9$ cells/ml at day 5 or 6 of incubation when the fermentation was stopped.

During all fermentation experiments the temperature was controlled at about 29° C. The medium was aerated with headspace airflow, and the dissolved oxygen (pO$_2$) concentration was controlled by automatic variation of the agitation-rate, to maintain a set pO$_2$ concentration. Temperature, pH and pO$_2$ concentration were monitored online, but pH and foam formation were not controlled.

In comparative experiments up to 4 fermenters were run in parallel, which started off simultaneously with the same medium and *Leptospira* inoculum. One fermenter then usually contained only standard EMJH medium and served as reference, while in the others different supplementations of polyunsaturated C18 fatty acid were made.

1.1.3 Supplementation with Linoleic Acid

Supplementation was done either with pure linoleic acid (Sigma Aldrich, >99% pure) as a 10% v/v stock in absolute ethanol (JT Baker). Alternatively, linoleic acid was supplemented by using a BSA that was created with a high level of linoleic acid (high LA BSA). This high LA BSA was used either to replace a standard BSA in EMJH medium, or was used in addition to BSA in the EMJH medium, in which case it was added as a 25% w/v stock solution in sterile water. The high LA BSA or the pure linoleic acid/ethanol supplements were fed to a fermenter over the course of 4 hours, at 0.1-0.2 ml/hour, until the fermenter culture had received a desired total amount of linoleic acid. Different total available levels of linoleic acid have been tested, of between about 5 and 425 μg/ml in the total volume. The fermenter cultures of *Leptospira* were supplemented at different cell-densities i.e. at early-, mid- or end phase culture. Typical mid-phase cell density was at about 5×10^8 cells/ml, which was reached during day 2 of the main incubation. Upon supplementation with linoleic acid from the pure linoleic acid in ethanol stock, sometimes a small decrease in pH was noted, which was corrected by applying some NaOH.

1.1.4 Sampling and Off-line Analyses

Daily 5 ml samples were taken aseptically, directly from the fermenter, for analyses of total cell count (by Petroff-Hausser counting chamber); antigenic mass (by antigen amount Elisa); inactivated cells; and for profiling of the fatty acid type and-relative amounts (by gas chromatography) in the culture medium.

Samples were inactivated with 0.1 or 0.2% v/v BPL, at 29° C. for 16-24 hours. The inactivated *Leptospira* were tested in an antigen Elisa within 24 hours.

1.2. Antigen Elisa

The antigenic mass of *Leptospira* LPS antigen was determined in antigen Elisa's, which were based on a set of serogroup-, or serovar specific, agglutinating, mouse monoclonal antibodies (moabs), which had been obtained from the: WHO/FAO/OIE and National Collaborating Centre for Reference and Research on Leptospirosis, Department of Biomedical Research, Royal Tropical Institute, Amsterdam, The Netherlands. The moabs used are listed in Table 2. For a reference see: R. A. Hartskeerl et al., (International course on laboratory methods for the diagnosis of Leptospirosis, 4th Edition, 1 Apr. 2004. Royal Tropical Institute, Amsterdam).

The Elisa's were set up as capture assays, whereby the same moab was used for coating and for detection.

TABLE 2

Moabs used for the antigen Elisa of *L. interrogans* (sensu lato).

| serogroup | serovar | moab |
|---|---|---|
| Canicola | Portland-vere | F152C11 |
| Icterohaemorrhagiae | Copenhageni | F12C3 |
| Australis | Bratislava | F81C3 |
| Grippotyphosa | Dadas | F71C9 |
| Pomona | Pomona | F43C9 |
| Tarassovi | Gatuni | F151C8 |
| Sejroe | Hardjo | F22C6 |

1.2.1 Preparation of Monoclonal Antibodies for Coating

The moabs for use in the antigen Elisa could be derived from ascites or from cell culture. Both types were purified prior to use by a standard non-chromatographic method. In short: albumin and other non-IgG proteins were precipitated with caprylic acid. Next, the IgG fraction was precipitated with ammonium sulphate. With this method it was possible to isolate more than 80% of the IgG with a purity equal to IgG purified by anion-exchange chromatography.

Alternatively, the moabs could be purified by protein-G column chromatography.

1.2.2 Preparing Conjugated Monoclonal Antibodies

For the antigen Elisa's Horse Radish Peroxidase (HRP)-IgG conjugates were prepared from the moabs, using standard procedures. Basically, the reaction involved a periodate oxidation of the carbohydrate residues of the HRP enzyme to form aldehyde groups, which subsequently reacted with free amino groups on the monoclonal IgG molecules.

1.2.3 Preparation of Antigen Amount Reference Standards

A reference standard was prepared for each *Leptospira* strain that was tested by antigen Elisa. The standard is a batch of monovalent *Leptospira* antigen, from inactivated cells. This was prepared using common techniques, essentially by proliferating a specific strain of *Leptospira* in EMJH medium as described above, and was inactivated as described before. Next the standard was concentrated and/or diluted in phosphate buffered saline, to contain about 1×10^9 cells/ml. An arbitrary number of antigen units was affixed to the sample, for example: 1000 Units/ml. When the standard needed replenishing, a subsequent preparation of the same standard, was compared and titrated alongside the old standard several times, before replacing it.

1.3. Fatty Acid Analysis

Fatty acid compositions and -amounts were tested from samples of *Leptospira* cells, culture medium components, and from complete EMJH culture medium samples, according to well-known procedures. The extraction of fatty acids was done as published by Bligh & Dyer (1959, Can. J. of Biochem. Physiol., vol. 37, p. 911) and Morrison & Smith (1964, J. of Lipid Res., vol. 5, p. 600). In short: a 0.5 ml sample was tested, containing either pure complete culture medium, or a sample diluted in water: of *Leptospira* cells (between 1×10^9 and 1×10^10 per 0.5 ml; the cells had been BPL inactivated), or of 1% w/v of a BSA sample. This 0.5 ml was extracted with 1 ml of methanol and 2 ml of chloroform, by mixing for 3 minutes. Another 0.5 ml of water was added, mixed for 30 sec., and the sample was centrifuged for 10 min. at 1.000×g at 2-8° C. The 2 ml chloroform (lower) phase was transferred to a glass vial, and the chloroform was dried off under an $N_2$ gas stream. The dried lipids were re-dissolved in 0.6 ml BF3 in methanol, and heated for 15 min. at 95° C., which methylated the fatty acids. Next 0.3 ml water and 0.3 ml hexane were added, this was mixed by shaking, after which the hexane (upper) phase was transferred to a standard gas chromatography set-up for analysis of the profile, and the relative amounts of the fatty acids in the extract. As internal standard a sample of C21:0 fatty acid (Heneicosylic acid) of known concentration was used. Normally the samples were measured in duplo, and samples were prepared and measured in containers of glass.

2. Comparison of Prior Art Proliferation Conditions

As a comparative example, the formation of antigenic mass in a Leptospira batch culture under standard prior art conditions (thus without supplementation) was analysed. Leptospira of serogroup lcterohaemorrhagiae were cultured in standard EMJH medium, that had been completed with polysorbate 80 (Croda), and a standard commercial BSA (Millipore). After several rounds of pre-proliferation a main fermenter culture was inoculated and run for 5 or 6 days. For *Leptospira* of serogroup lcterohaemorrhagiae, the antigenic mass obtained in these conditions of proliferation, was usually between 500 and 700 Antigen Units (of serogroup lcterohaemorrhagiae) per 1×10^9 cells, as the average over days 3-5, when the culture was stationary.

When such a batch of *Leptospira* antigen was tested in an in house in vitro potency assay, it failed to reach the required minimal potency level.

This problem was not solved by using in EMJH medium a commercial BSA that was specially recommended for *Leptospira* culture: BovoLep® BSA (Bovogen, Australia). This was tested next to BovoStar®, which is a standard all-purpose BSA from the same manufacturer, and next to the BSA (Millipore) that was used before. Results are presented in Table 3. "na" is: not available.

Interestingly , BovoLep® did increase the biomass of *Leptospira*, as advertised, but it had no significant effect on their antigenic mass. This typifies the classical approach to *Leptospira* proliferation up till today: a focus on the biomass levels.

TABLE 3

Results from use of different BSA ingredients in EMJH medium:

| fermenter conditions | C18:2 total conc. μg/ml | Cell numbers at 3 days | Ag U/10^9 cells/ml, at 3 days |
|---|---|---|---|
| BSA, Millipore | 5 | 1.6 × 10^9 | 525 |
| BSA, BovoStar ® | na | 1.6 × 10^9 | 533 |
| BSA, BovoLep ® | na | 1.8 × 10^9 | 498 |

3. Effect of Polyunsaturated C18 Fatty Acid 3.1. Linoleic Acid

Only when more linoleic acid (C18:2) was made available to *Leptospira* cultures, did the antigenic mass increase.

The standard EMJH medium as tested and described above was found to provide about 5 μg/ml of linoleic acid (see Table 3). This was mainly derived from the 0.125% polysorbate 80, as the 1% standard BSA provided less than 1 μg/ml linoleic acid, close to the detection limit of the gas chromatographic analysis.

In this respect, Polysorbate 80, as defined by the Pharmacopeia, is allowed to contain linoleic acid to a maximum of 18% of its fatty acids. However in practice it was found to carry much less, typically less than 1.5 %. From one common type of polysorbate 80 (type: Vegetable Grade, from: Croda, France) the inventors compared the linoleic acid content from 48 batches over several years, and found that the average amount of linoleic acid was about 0.3% w/w of total fatty acids. Assuming that polysorbate 80 consists essentially of fatty acids, then the 0.125% v/v of polysorbate 80 that is used in EMJH medium, provides about 4 μg/ml linoleic acid to the culture.

A BSA was created that comprised an increased amount of linoleic acid. Use of this high LA BSA at 1% w/v in EMJH medium provided about 21 μg/ml linoleic acid to a *Leptospira* culture; with the contribution of the polysorbate such a culture medium provided 25 μg/ml linoleic acid to a fermenter culture of *Leptospira*. This increase in the available linoleic acid amount, strongly increased the generation of *Leptospira* antigen, to an antigenic mass of 1636 Ag U/1×10^9 cells (average of days 3-5).

This way the inventors have demonstrated the utility of their discovery: the antigenic mass of a *Leptospira* culture could be increased with 124%, when a *Leptospira* culture was supplemented with 25 instead of with 5 μg/ml linoleic acid.

FIGS. 1 and 2 depict the results of analyses of daily samples from a proliferating *Leptospira* culture with linoleic acid supplementation, using high LA BSA in the EMJH medium. In FIG. 1 the biomass (left vertical axis) showed a steady increase over all six days of proliferation. The antigen amount (right vertical axis) reached much higher levels than could be obtained from using standard BSA in the culture medium. Nevertheless, the antigenic mass did not increase much after day three. FIG. 2 displays the reason, in the fatty acid profile of the medium from this culture, which clearly demonstrates the relevance of linoleic acid in this context; results are in % w/w of total fatty acids. Please note that the levels of C16:0 (palmitic acid), C18:0 (stearic acid), and C18:1 (oleic acid) relate to the left vertical axis, while the level of C18:2 (linoleic acid) relates to the right vertical axis.

FIG. 2 displays essentially unchanged amounts of C16:0, C18:0, and C18:1 fatty acids in the culture medium over the course of the culture, whereby C18:1, from polysorbate 80, forms the bulk of the total amount of fatty acid. However, the level of C18:2 shows a strong drop over the first three days, and is below the detection limit(≤0.3%) on days 3-5. The exhaustion of the linoleic acid coincides with the reduction of the increase in antigen generation, as shown in FIG. 1.

3.2. Linolenic Acid

Neither of the isoforms of linolenic acid (C18:3): alpha- or gamma-, could be detected above the detection limit of the gas chromatography (about 0.6 μg/ml of fatty acid), in batches of BSA or of polysorbate 80. Consequently, standard complete EMJH culture medium does not contains any significant amounts of C18:3. As a result, in experiments where supplementation of a linolenic acid to a *Leptospira* culture was tested, essentially all of the linolenic acid that was made available to the culture, derived from the linolenic acid that had been supplemented to the culture by separate addition.

4. Further Supplementation of Linoleic Acid to a *Leptospira* Culture

If further linoleic acid (C18:2) was supplemented, the antigenic mass could be further increased.

In a similar culture as described above, linoleic acid was supplemented at mid-exponential phase, on day 2, with pure linoleic acid, diluted in ethanol. An amount of linoleic acid was added that provided 100 μg/ml linoleic acid in the culture. As the fatty acid profiling of FIG. 3 displays, after the rapid initial decrease, and the clear spike resulting from the supplementation on day 2, linoleic acid levels steadily decreased again upon continuation of the culture. The levels of C16:0 and C18:1 fatty acids were assayed as internal references, but these were largely unchanged as expected.

The antigenic mass produced in this experiment for *Leptospira* from serogroup Icterohaemorrhagiae was 1767 Ag. U/1×10^9 cells (average of days 3-5).

5. Comparative Cultures with Different Supplementation Conditions

In more elaborate experiments, of the same set-up as in previous Examples, comparative fermenter cultures of *Leptospira* from serogroup Icterohaemorrhagiae were run side by side, wherein different conditions of linoleic acid (C18:2) supplementation were compared. To highlight the effect of the linoleic acid supplementation, a standard BSA was used in the EMJH medium. In some fermenters linoleic acid was supplemented in mid-exponential phase, either in pure form in ethanol, or as a complex to BSA, by addition of a solution of a high LA BSA.

The amounts of linoleic acid supplemented were 50, 75 and 150 μg/ml. Table 4 lists also the total amount of linoleic acid made available to the cultures.

For all fermenters, daily samples of cells and medium were taken and analysed. Results are presented in FIGS. 4 and 5, and in Table 4 below. The antigenic mass values are based on averages for days 3-5 of the cultures. Also the relative increase in antigenic mass for the different supplementations is expressed as a percentage relative to the un-supplemented culture with standard BSA. The term "non-supplemented" refers to a culture employing standard BSA in EMJH.

TABLE 4

Effect on Leptospira antigenic mass from different supplementations with linoleic acid

| fermenter conditions | C18:2 total conc. μg/ml | Ag. mass, average of days 3-5 Ag. U/10^9 cells/ml | relative Ag. mass (%) |
|---|---|---|---|
| non-supplemented, stand. BSA | 5 | 729 | 100 |
| supplem. pure C18:2, 75 | 80 | 1450 | 199 |
| supplem. pure C18:2, 150 | 155 | 1550 | 213 |
| supplem. high LA BSA, 50 | 55 | 1612 | 221 |

Figure 4:
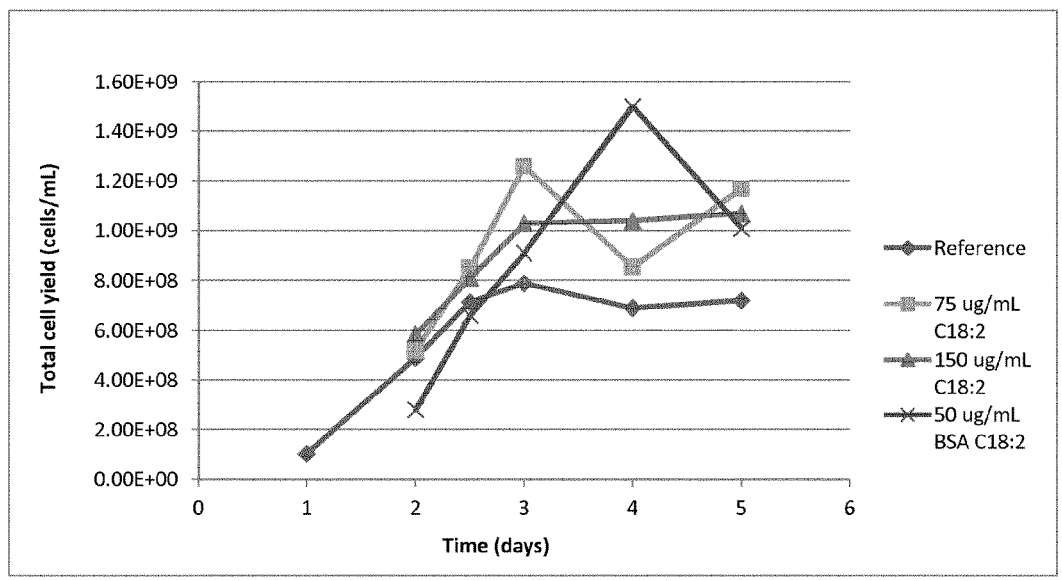

As is clear from Table 4, and from the corresponding graphs in FIGS. 4 (biomass) and 5 (antigen amount), there is a rapid and significant increase in the antigenic mass of *Leptospira* when the culture is supplemented with linoleic acid, which is not observed in an un-supplemented culture. Some increase in biomass occurs upon supplementation of linoleic acid, but the increase in antigenic mass exceeds that significantly. The increase in antigenic mass is somewhat higher when the culture is supplemented with 150 μg/ml, as compared to supplementation with 75 μg/ml. However, there was not much difference between when the linoleic acid was supplemented in pure form, or as complex with BSA. Possibly this is a trade-off between increase of antigenic mass versus some toxicity.

Figure 5:
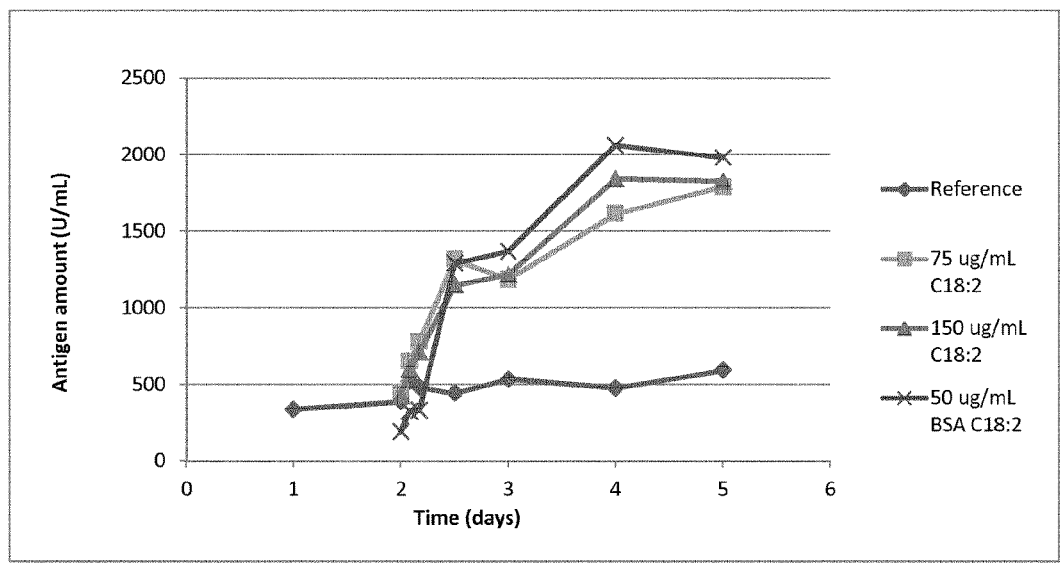

Further favourable effects can be deduced from FIG. 5: an increased antigenic mass can now be reached much quicker through supplementation with linoleic acid. For example, FIG. 5 shows that with supplementation of linoleic acid, a high antigenic mass can be reached within hours from the supplementation.

Also, when the maximal antigenic mass levels that were finally obtained are compared, it is evident that when supplemented cultures are run for the same length of time as previously, then considerably increased amounts of antigenic mass can be obtained.

6. Confirmation of Supplementation Effect of Linoleic Acid in *Leptospira* of Different Serogroups In a next study it was confirmed that the increase in antigenic mass upon supplementation with linoleic acid (C18:2) is a general phenomenon in *Leptospira*. In several experiments cultures of *Leptospira* strains from several serogroups were proliferated in fermenters in similar set-ups as before and with a similar supplementation: in EMJH medium with either standard BSA or with high LA BSA; some cultures were further supplemented with 100 μg/ml linoleic acid, from pure linoleic acid in ethanol. Results of analyses of biomass and antigen amount are presented in FIGS. 6-7 (Sejroe), and 8-9 (Grippotyphosa), and are summarised in Table 5.

For *Leptospira* from serogroup Sejroe (serovar Hardjo), supplementation with 100 μg/ml linoleic acid of high LA BSA culture medium resulted in an increase of the antigenic mass with an impressive 184%. Some increase in biomass was observed after supplementation, but the increase in antigen amount was much higher. The fermenter was run for 6 days, and scores for these experiments were averaged over days 5 and 6 of the culture.

For serogroup Grippotyphosa the scores were averaged over days 4 and 5 of the culture. An increase with 63% was observed in the antigenic mass, resulting from the supplementation with linoleic acid.

Similarly, for serogroup Australis (serovar Bratislava), an increase in antigenic mass with 45% was observed; here the low LA BSA medium was used for supplementation.

TABLE 5

Confirmation of effect on antigenic mass by supplementation with linoleic acid for Leptospira from different serogroups

| Serogroup | fermenter conditions | C18:2 total conc. μg/ml | Antigenic mass, 2 day average Ag. U/10^9 cells/ml | relative Ag. mass (%) |
|---|---|---|---|---|
| Sejroe | non-supplemented | 5 | — | — |
| | high LA BSA | 25 | 287 | 100 |
| | supl. pure C18:2, 100 | 125 | 814 | 284 |
| Grippotyphosa | non-supplemented | 5 | — | — |
| | high LA BSA | 25 | 5074 | 100 |
| | supl. pure C18:2, 100 | 125 | 8286 | 163 |
| Australis | non-supplemented | 5 | 8862 | 100 |
| | high LA BSA | 25 | — | — |
| | supl. pure C18:2, 100 | 105 | 12822 | 145 |

6.1. Supplementation of *Leptospira* Serogroup Tarassovi

In a supplementation similar to that described in Example 6 above, the effect of supplementation with different amounts of C18:2 fatty acid on the biomass and the antigenic mass of a culture of *Leptospira* serogroup Tarassovi in EMJH medium with standard BSA was tested. Results are presented in FIGS. 11 and 12.

Whereas supplementation with 300 μg/ml C18:2 turned out to be toxic to this culture, the supplementation with 100 or 200 μg/ml C18:2 did produce strong increases in antigenic mass per unit of biomass: of 67% respectively 99%, compared to the unsupplemented reference culture.

7. Maximum Supplementation Levels

In one study the maximal level of linoleic acid (C18:2) supplementation was investigated: Leptospira from serogroup lcterohaemorrhagiae were cultured in EMJH with high LA BSA, and supplemented with additional 100, 200 or 400 μg/ml linoleic acid, from pure linoleic acid in ethanol. From the results it was apparent that the addition of 400 μg/ml induced toxicity for the bacteria, as cell numbers decreased rapidly after supplementation. Therefore this experiment will be repeated by giving a similarly high level of linoleic acid supplementation, but then from linoleic acid in a complex with BSA that has been saturated with linoleic acid. The stimulatory effect of the 100 μg/ml supplemented group was as observed before, while the 200 μg/ml group gave slightly less increase of the antigenic mass compared to that of the 100 μg/ml group.

Consequently, under these conditions supplementation with pure linoleic acid seems to be optimal when between 25 and 250 μg/ml linoleic acid is made available to a culture of *Leptospira*.

8. Time Point for Supplementation

In further experiments the relevance of the time point for the supplementation of a *Leptospira* culture was determined. Using *Leptospira* of serogroup lcterohaemorrhagiae, supplementation-time points tested were early-, mid-and late exponential phases. EMJH medium with standard BSA was supplemented with 100 μg/ml pure linoleic acid in ethanol. The total amount of linoleic acid made available to these cultures was therefore 105 μg/ml.

Results are presented in Table 6 and FIG. 10. As FIG. 10 demonstrates, an acute increase in antigenic mass can be induced at all phases of the *Leptospira* culture, with a very rapid climb already at 2, 4, and 8 hours after the supplementation. With this time scale, the increase results mostly from a biochemical process, and less from proliferation.

The fact that the amount of antigen produced seems to be lower when the supplementation is done later, derives from the slight positive effect that the linoleic acid supplementation has on the biomass. This is levelled out when expressing the antigenic mass per standard cell amount, see Table 6.

TABLE 6

Effect of linoleic acid supplementation at different phases of proliferation of a Leptospira culture.

| | | Ag. mass, average of days 4-5 | |
|---|---|---|---|
| fermenter conditions | C18:2 total conc. μg/ml | Ag U/10^9 cells/ml | relative Ag. mass (%) |
| non-supplemented, low LA BSA | 5 | 789 | 100 |
| 1 × 10^8 cells/ml, 100 | 105 | 1783 | 226 |
| 5 × 10^8 cells/ml, 100 | 105 | 1564 | 198 |
| 9 × 10^8 cells/ml, 100 | 105 | 1656 | 210 |

Tests of supplementation at further time points: after harvest, after wash and after concentration, are on-going. The incubation of end phase cultures may require medium refreshment; nevertheless the supplementation of an end phase culture is estimated to be most favourable, because in that stage the cells are in high numbers, and are still capable of antigenic mass formation. In addition in this stage it is less relevant if any residual toxicity of the supplemented linoleic acid would interfere with the cells' capacity to proliferate as that is no longer required.

9. Determination of Improved Immuno-potency of Vaccines Prepared from Supplemented *Leptospira* Cultures

*Leptospira* cultures that were supplemented with linoleic acid have been produced, as described above. These will be formulated into inactivated adjuvated Leptospirosis vaccines as is well known in the art, and tested in in vivo experiments as prescribed in the Pharmacopeia monographs. Effects of seroresponse, challenge protection, and level of adverse vaccination reactions will be monitored.

Because for Leptospirosis vaccines the correlation between antigenic mass and immuno-protective capacity is well known, it can be predicted with certainty that bacterin vaccines having a higher antigenic mass than previously, will also induce higher levels of immune-protection.

Similarly, because the protein load of *Leptospira* bacterin vaccines is clearly implicated as the causative effect of vaccination side-effects, it can also be predicted that *Leptospira* bacterin vaccines having less protein, but equal antigenic mass as previously, will induce fewer side effects, but an equal, or probably improved, immunisation.

10. Supplementation of *Leptospira* Cultures with a Linolenic Acid

Supplementation of *Leptospira* cultures with a linolenic acid (C18;3), either alpha-or gamma-, was done essentially as described above for supplementation with linoleic acid (C18:2). Results were also largely comparable, except for instances were a particular *Leptospira* displayed a particular preference for one form of polyunsaturated C18 fatty acid over others.

The antigenic mass per unit of biomass, was also calculated in a similar way, over the days where the culture of *Leptospira* was stationary; typically this was at days 3-4-5 post inoculation, occasionally and for some serogroups that was at days 4-5-6 after inoculation. As before, the average antigenic mass score by Elisa was calculated per 1×10^9 cells (pre-inactivation). The relative increase in antigenic mass was calculated in relation to the reference culture, which did not receive supplementation. The average antigenic mass 1×10^9 cells of the reference culture was set at 0% increase.

In all experiments with supplementation of *Leptospira* cultures with C18:3, the EMJH had been prepared using a standard BSA (Milipore), and polysorbate 80 (Croda). As described, such EMJH medium of itself contained negligible amounts of C18:3.

Both alpha-and gamma C18:3 were purchased as pure chemicals (>98%). Shortly before use for supplementation, they were diluted in pure ethanol to 10% or 20% v/v, depending on the amount of C18:3 that was to be added to a culture. This dilution in ethanol was added to a *Leptospira* culture by addition in 5 doses, divided over a period of 4 hours.

10.1. Consumption of Linolenic Acid in *Leptospira* Cultures

In line with what is described for C18:2 in Example 4, and FIGS. 1-3, the consumption of C18:3, with and without supplementation was studied. Results for a culture of *Leptospira* serogroup *Icterohaemorrhagiae* in EMJH medium are presented in FIGS. 13 and 14. The standard biomass expansion of these cultures was similar to that presented in FIG. 1.

FIG. 13 presents the profile of relative amounts of the major fatty acids in an unsupplemented culture: C16:0 and C18:1, these are presented relative to the left side vertical axis, and remain relatively constant, even when the culture is expanding. Amounts of C18:2 and C18:3 are presented relative to the right side vertical axis: at day 3, the levels of C18:2 have already been exhausted, and levels of C18:3-alpha are steadily declining, and are exhausted from day 5 onwards.

Figure 14:
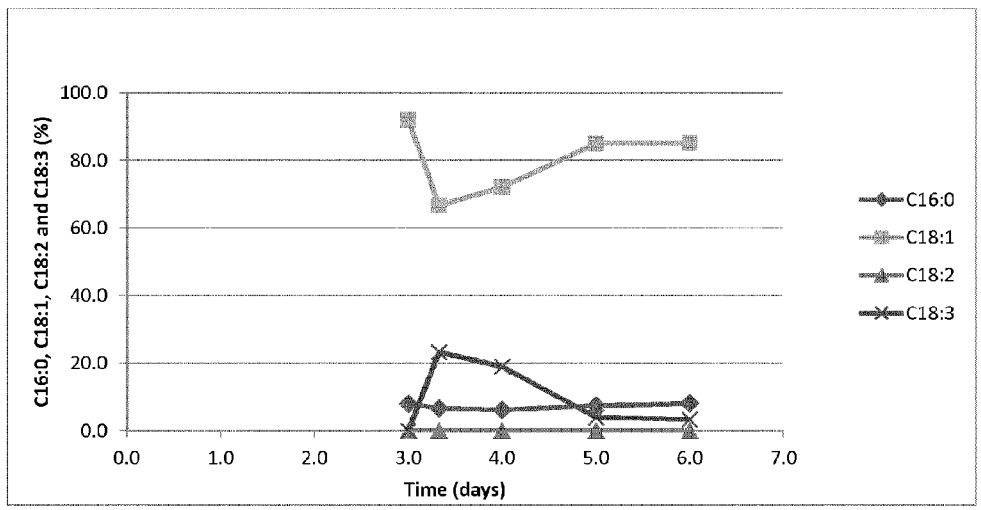

FIG. 14 presents a similar profile, but of a culture that was supplemented with 200 µg/ml alpha C18:3 at day 3 post inoculation. In this figure all relative amounts of fatty acid are presented based on the left side vertical axis. As can be seen, the supplementation of alpha C18:3 results in a clearly detectable level of C18:3 by the day 3.3 sampling point. In subsequent days, this amount is steadily consumed, and is again exhausted at day 5. The corresponding increase in antigenic mass is displayed in the FIGS. 16, 18, and 20.

10.2. Effect of Supplementation of Different Amounts of C18:3

Comparable to what is described for C18:2 in Example 5, and FIGS. 4 and 5, a culture of *Leptospira* serogroup lcterohaemorrhagiae in EMJH medium was supplemented with different amounts of C18:3, either alpha-linolenic acid (alpha C18:3) or gamma-linolenic acid (gamma C18:3). Results are presented in FIGS. 15-20.

As is clear in all these results: supplementation with a linolenic acid induces in a *Leptospira* culture an increase in antigenic mass which strongly exceeds an increase in biomass, producing a net increase in antigenic mass per unit of biomass.

Figure 15:
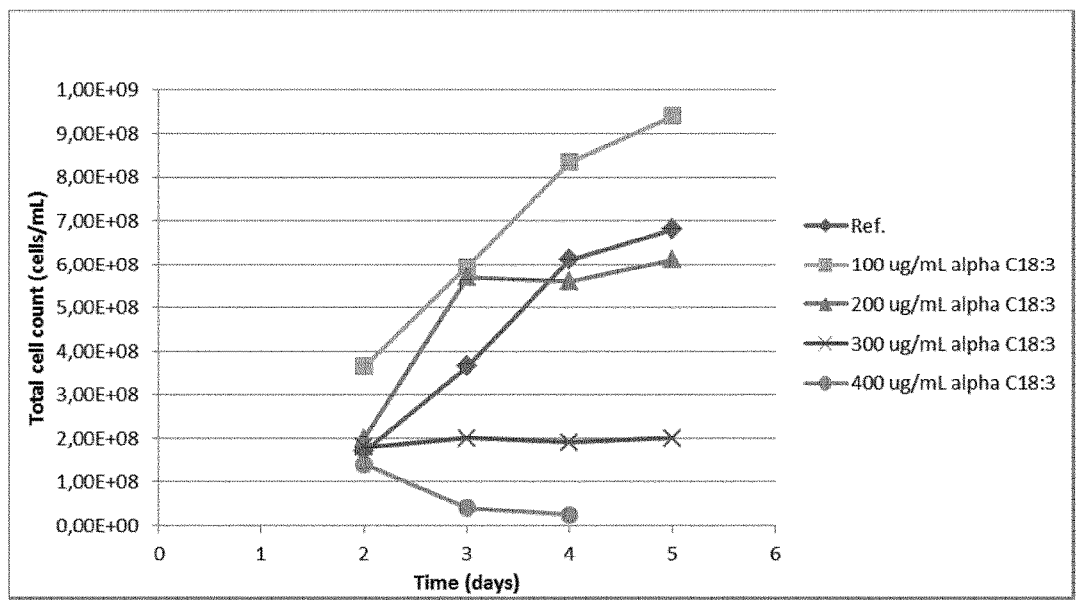
Figure 16:
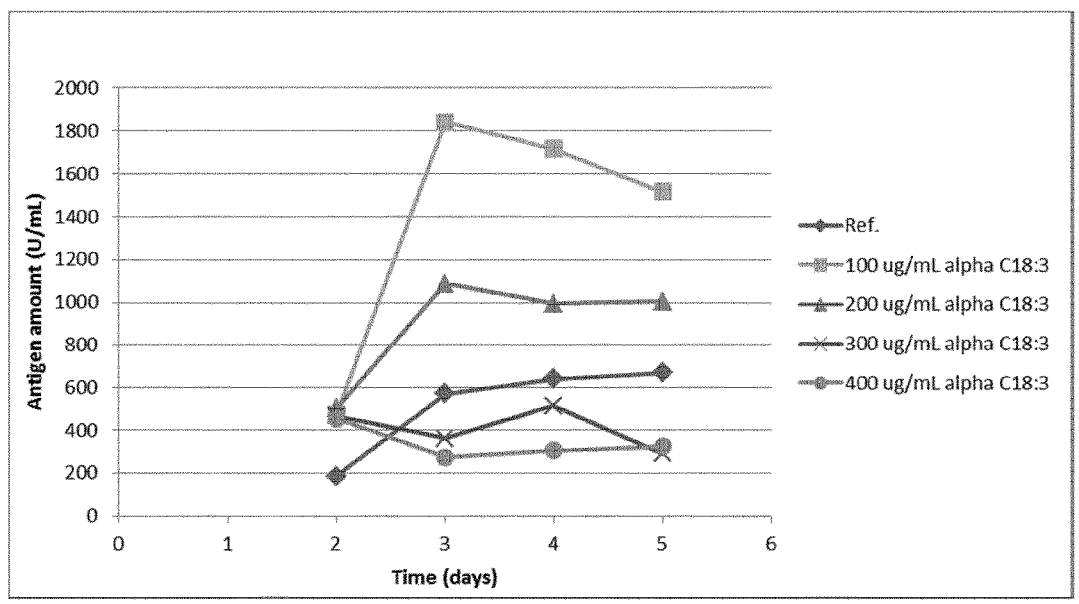

FIGS. 15 and 16 display the effects on biomass and on antigenic mass of supplementation with 100, 200, 300, or 400 µg/ml alpha C18:3. Clearly the supplementation of 300 or 400 µg/ml had toxic effects on the culture. For the other amounts, 100 µg/ml alpha C18:3 gave a slightly better increase in antigenic mass: 122%, over 200 µg/ml alpha C18:3: 81%.

Figure 17:
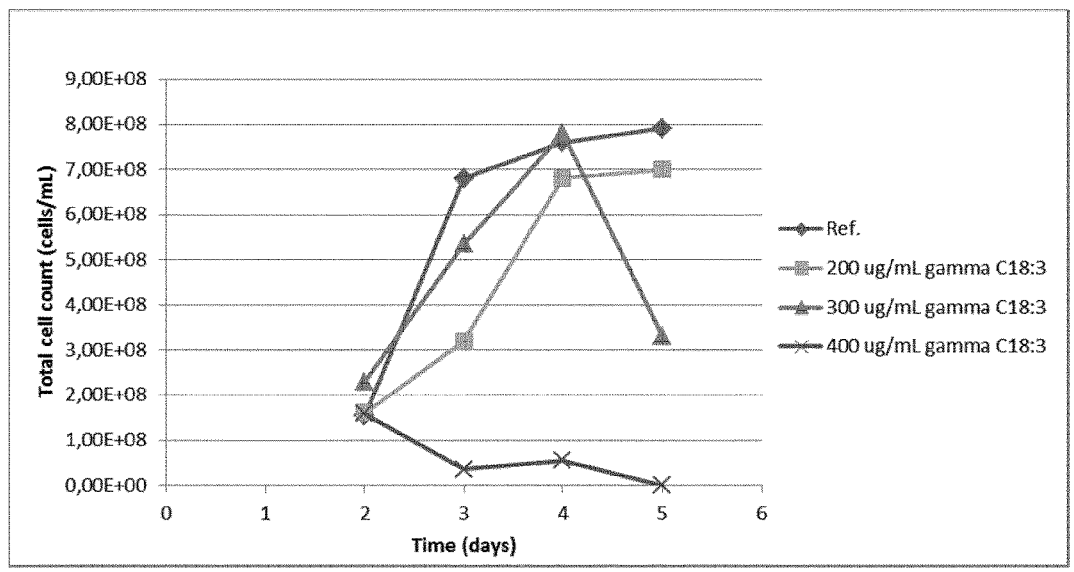
Figure 18:
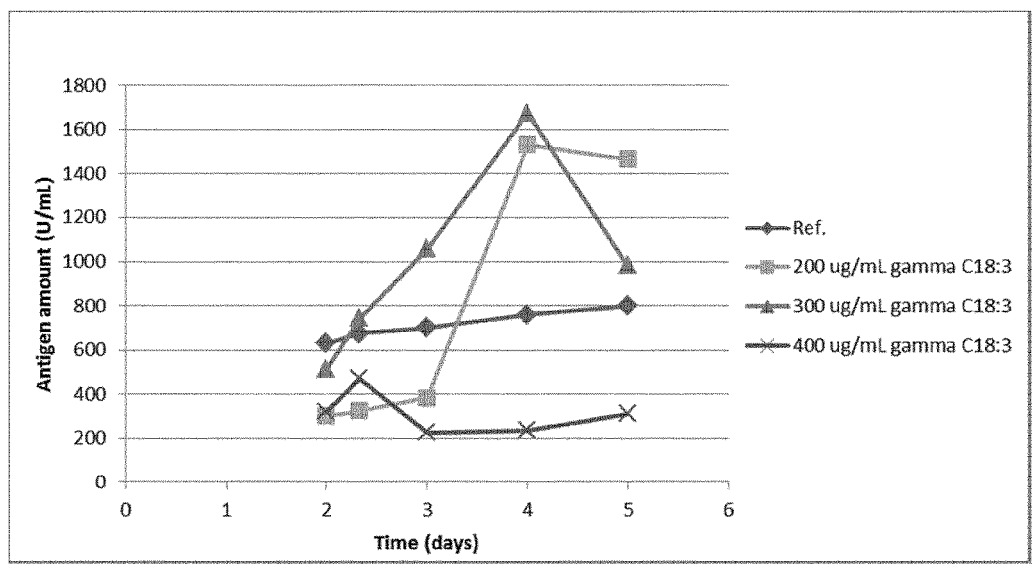

FIGS. 17 and 18 display the effects on biomass and on antigenic mass of supplementation with 200, 300, or 400 µg/ml gamma C18:3. Apparently the gamma C18:3 was better tolerated by the *Icterohaemorrhagiae* culture than alpha C18:3, as only the 400 µg/ml amount showed toxicity.

The supplementation with 200 µg/ml gamma C18:3 gave a slightly lower increase in antigenic mass than the supplementation with 300 µg/ml gamma C18:3: 114% versus 153%.

Figure 19:
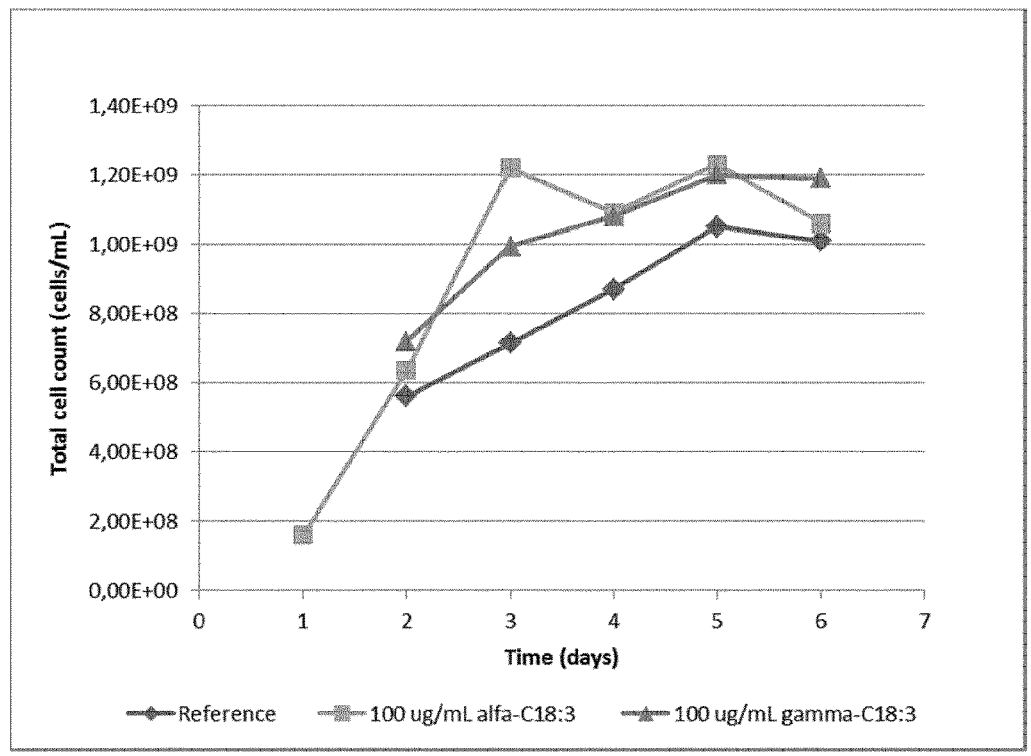
Figure 20:
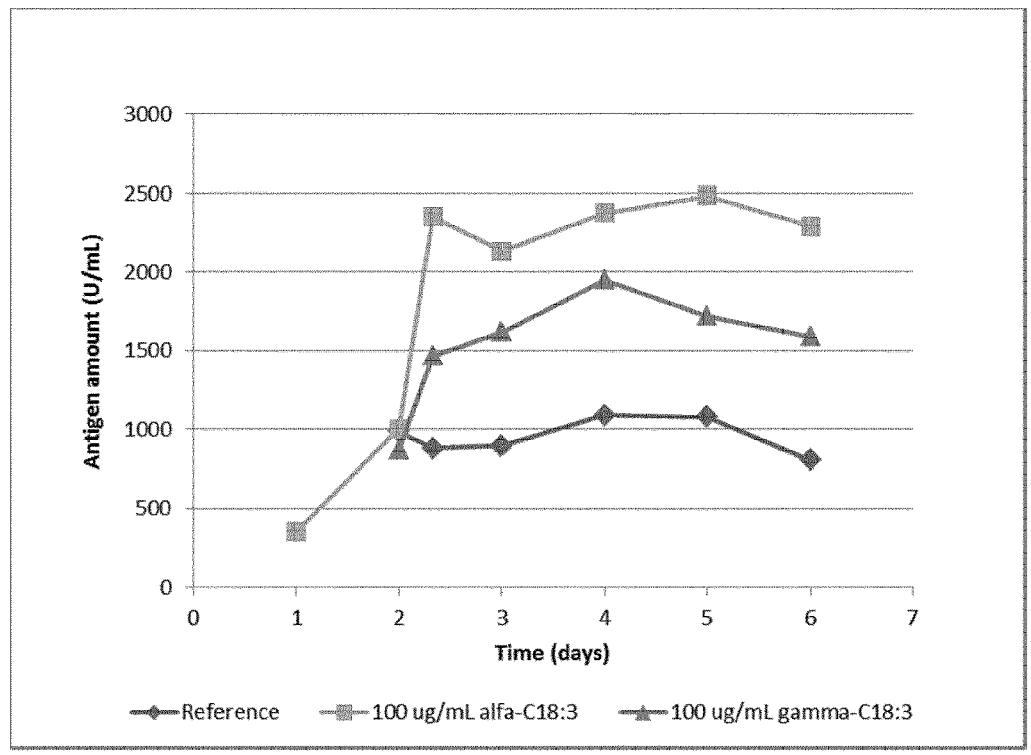

FIGS. 19 and 20 display a comparison of effects of an equal amount of alpha-or gamma C18:3, on biomass and antigenic mass of a culture of *Leptospira* serogroup lcterohaemorrhagiae in EMJH medium. A supplementation with 100 µg/ml alpha C18:3 induced a larger increase in relative antigenic mass than did 100 µg/ml gamma C18:3: 122% versus 170%.

This demonstrates the preference of serogroup lcterohaemorrhagiae *Leptospira* for the alpha isomer of C18:3.

10.3. Effect of C18:3 Supplementation of other *Leptospira* Serogroups

Comparable to what is described for C18:2 in Example 6, and FIGS. 6-9 and 11-12, the effect on antigenic mass by supplementation with a linolenic acid was also tested on *Leptospira* of serogroups other than lcterohaemorrhagiae. In particular cultures of serogroups Australis (serovar Bratislava), Tarassovi, Grippotyphosa, Pomona, or Canicola were tested, by supplementation with 100 or 200 µg/ml alpha C18:3, or with 100 µg/ml gamma C18:3. Results are presented in FIGS. 21-32, and in Tables 7 and 8.

TABLE 7

Effect of C18:3 supplementation on cultures of Leptospira from various serogroups

| | Relative increase in antigenic mass (%) | | | |
|---|---|---|---|---|
| Serogroup | 100 µg/ml alpha C18:3 | 200 µg/ml alpha C18:3 | 100 µg/ml gamma C18:3 | FIGS. |
| Australis (serovar Bratislava) | 40 | 62 | 15 | 21 and 22 |
| Tarassovi | 59 | 141 | 51 | 23 and 24 |
| Grippotyphosa | 60 | 63 | 57 | 25 and 26 |
| Pomona | 0 | 0 | 73 | 27 and 28 |

It was noted that *Leptospira* of the serogroups Australis, Tarassovi, and Grippotyphosa in general did not have a strong preference for either isomer of C18:3. However serogroup Pomona had a strong preference, namely for gamma C18:3; its antigenic mass generation was even less than the reference culture when alpha C18:3 was supplemented.

*Leptospira* of serogroup Canicola (strain WS 280503) were tested with several amounts of alpha-or gamma C18:3, as Canicola seemed to require (respectively: could tolerate) higher amounts of fatty acid before it displayed a relative increase in antigenic mass. Results are presented in FIGS. 29-32, and in Table 8.

TABLE 8

Effect of C18:3 supplementation of cultures of Leptospira serogroup Canicola

| Serogroup Canicola | Relative increase in antigenic mass (%) | FIGS. |
|---|---|---|
| 200 µg/ml alpha C18:3 | 107 | 29 and 30 |
| 300 µg/ml alpha C18:3 | 112 | |
| 400 µg/ml alpha C18:3 | 118 | |
| 200 µg/ml gamma C18:3 | 98 | 31 and 32 |
| 300 µg/ml gamma C18:3 | 83 | |

10.4. Maximal Supplementation Levels of C18:3

Comparable to what is described for C18:2 in Example 7, the effect of the amount of C18:3 that is supplemented seems limited in practice by its cytotoxicity for *Leptospira*. Although serogroup Canicola seemed to tolerate somewhat higher levels of C18:3 supplementation, most other serogroups showed cytotoxicity from 200 µg/ml C18:3 and up. There was no clear difference observed for the cytotoxicity from the alpha-or the gamma isomer of C18:3.

10.5. Time Point for Supplementation of C18:3

Figure 10:
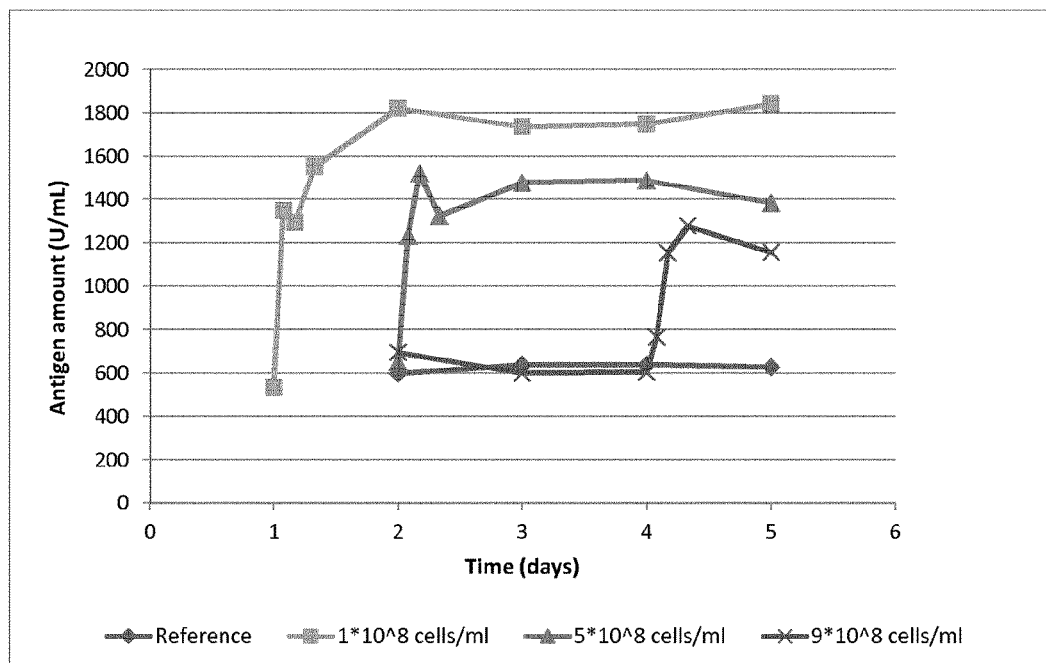

Comparable to what is described for C18:2 in Example 8, and FIG. 10, the effect of supplementation of a culture of *Leptospira* serogroup lcterohaemorrhagiae in EMJH medium, was tested with alpha-or gamma C18:3 at different time-points of the culture. Results are presented in FIGS. 33-36.

Figure 33:
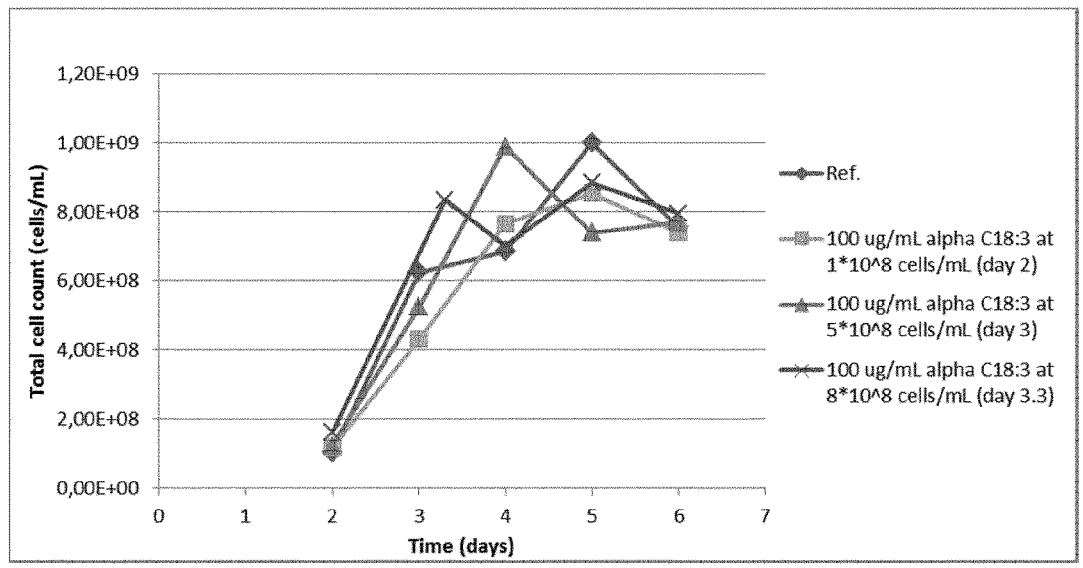
Figure 34:
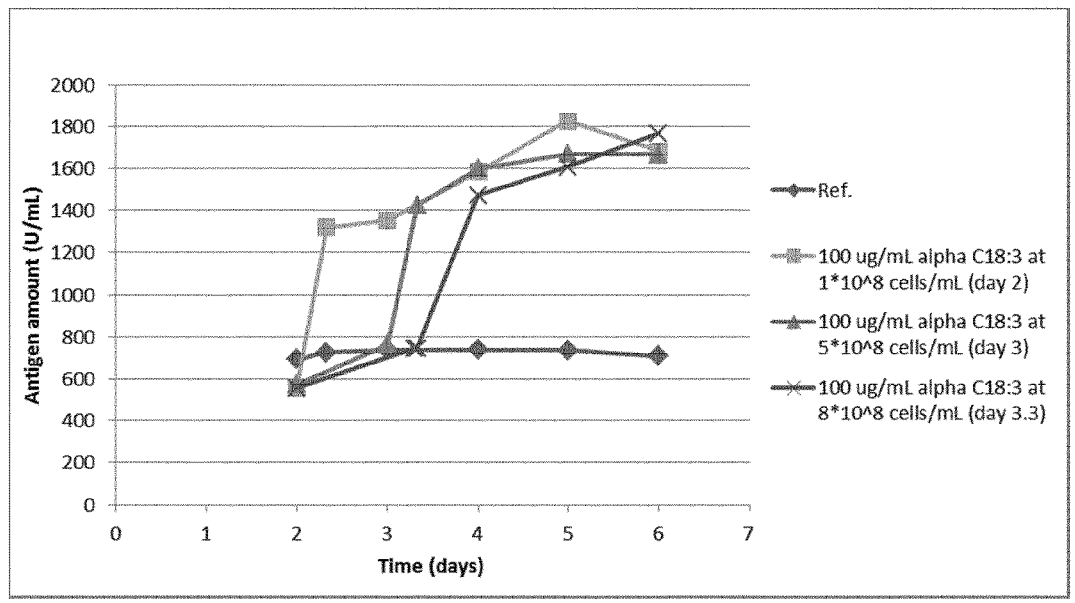

FIGS. 33 and 34 display the results of supplementation with alpha C18:3 at 1, 5, or 8×10^8 cells/ml. Relative increases in antigenic mass observed were: 163, 164, and 140%, respectively.

Figure 35:
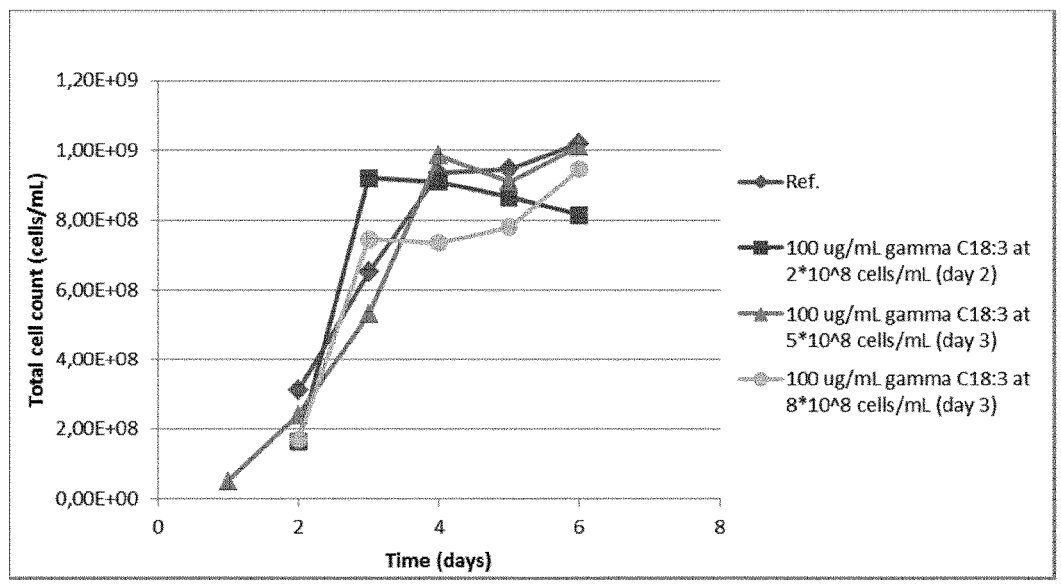
Figure 36:
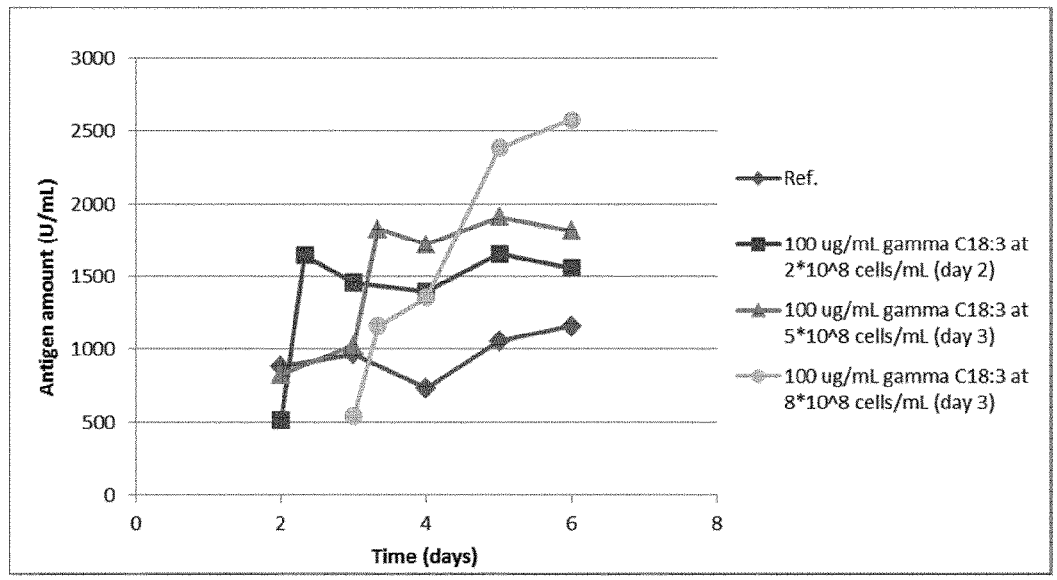

FIGS. 35 and 36 display the results of supplementation with gamma C18:3 at 2, 5, or 8×10^8 cells/ml. Relative increases in antigenic mass observed were: 71, 81, and 162%, respectively.

Consequently, the effect of the timing of the supplementation with C18:3, as a function of the cell-concentration at the moment of supplementation, does not seem very critical. Although supplementation with alpha C18:3 gave the highest increase in antigenic mass when applied at low-medium cell-concentration, while gamma C18:3 gave the highest increase when applied at high cell-concentration.

10.6. Combined Supplementation of Different Polyunsaturated C18 Fatty Acids

Surprisingly it was observed that polyunsaturated C18 fatty acids can also be combined in supplementation, and then cause a cumulative effect. This was tested with a culture of *Leptospira* serogroup lcterohaemorrhagiae in EMJH medium, that was supplemented with either 100 µg/ml 018:2, with 100 µg/ml alpha C18:3, or with the combination of 50 µg/ml C18:2 and 50 µg/ml alpha C18:3. The combination of fatty acids was provided to the culture by adding the two fatty acids as separate 10% dilutions in ethanol, practically simultaneous, in 5 additions over the course of 4 hours.

Increases in relative antigenic mass obtained were: 77%, 144% and 118% respectively. Results are displayed in FIGS. 37 and 38.

Remarkably the increase in antigenic mass obtained by supplementing with a combination of C18:2 and C18:3 produced a level of relative increase of antigenic mass (118%), that is very close to the arithmetic mean (111%) of the relative increases of the separate supplementations.

LEGEND TO THE FIGURES

FIG. 1:
Results of biomass and of antigen Elisa over time, on a culture of *Leptospira* from serogroup *Icterohaemorrhagiae* in EMJH medium containing high LA BSA that was not further supplemented.

Figure 2:
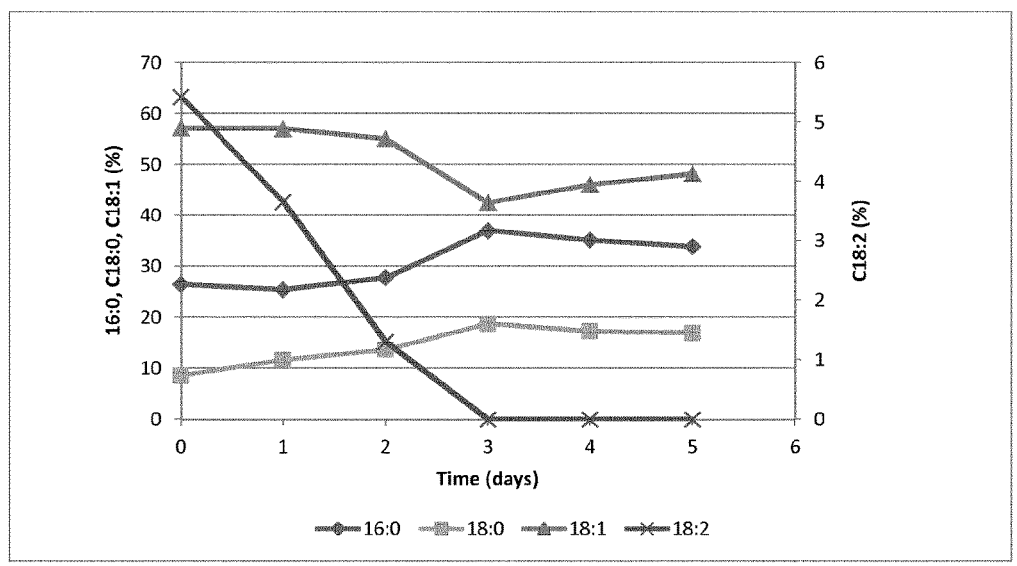

FIG. 2:
Results from analyses of the fatty acid profile in the culture medium of the culture represented in FIG. 1.

Figure 3:
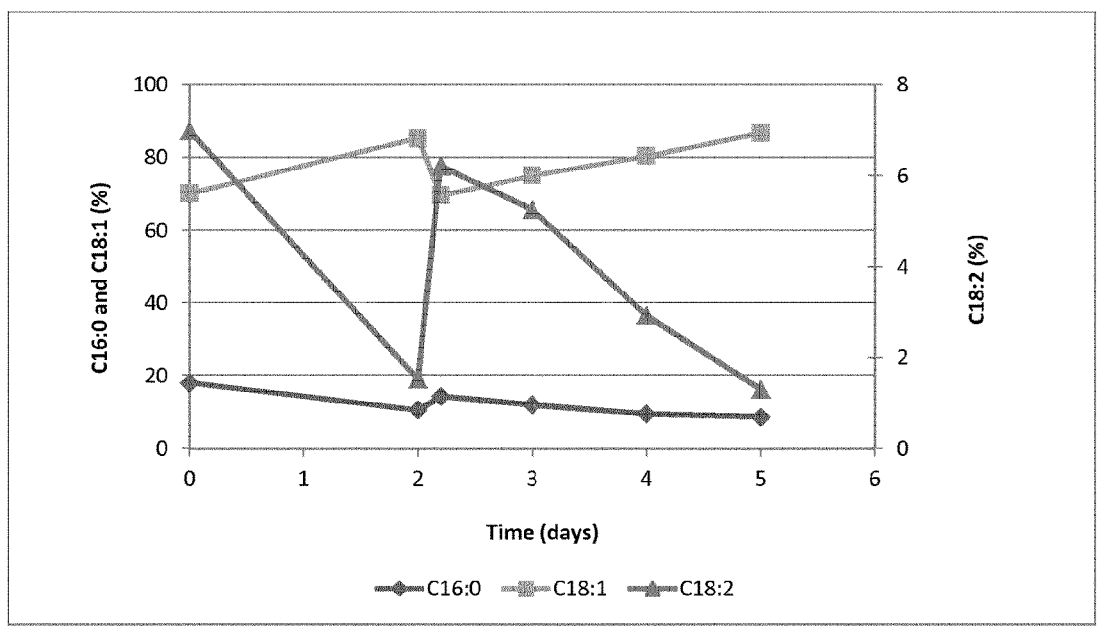

FIG. 3:
Fatty acid profile of the culture medium from a culture of *Leptospira* from serogroup *Icterohaemorrhagiae* in EMJH with high LA BSA, whereby the culture was supplemented with 100 µg/ml linoleic acid at a cell density of 5×10^8 cells/ml on day 2

FIGS. 4 and 5:
Respectively the biomass and the antigen amount measurement results from different cultures of *Leptospira* from serogroup lcterohaemorrhagiae, proliferated in EMJH medium with standard BSA; the cultures were either un-supplemented as reference culture, or supplemented with linoleic acid: one with 75 µg/ml of linoleic acid, from pure linoleic acid in ethanol; one with 150 µg/ml, also from pure linoleic in ethanol, and one with 50 µg/ml linoleic acid, as BSA-complexed linoleic acid.

Figure 6:
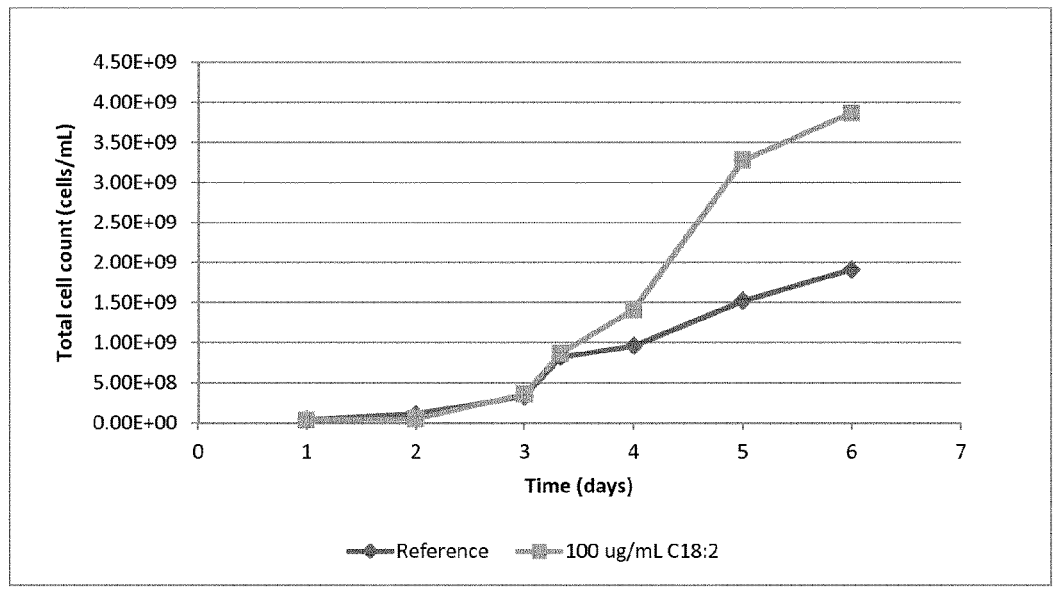
Figure 7:
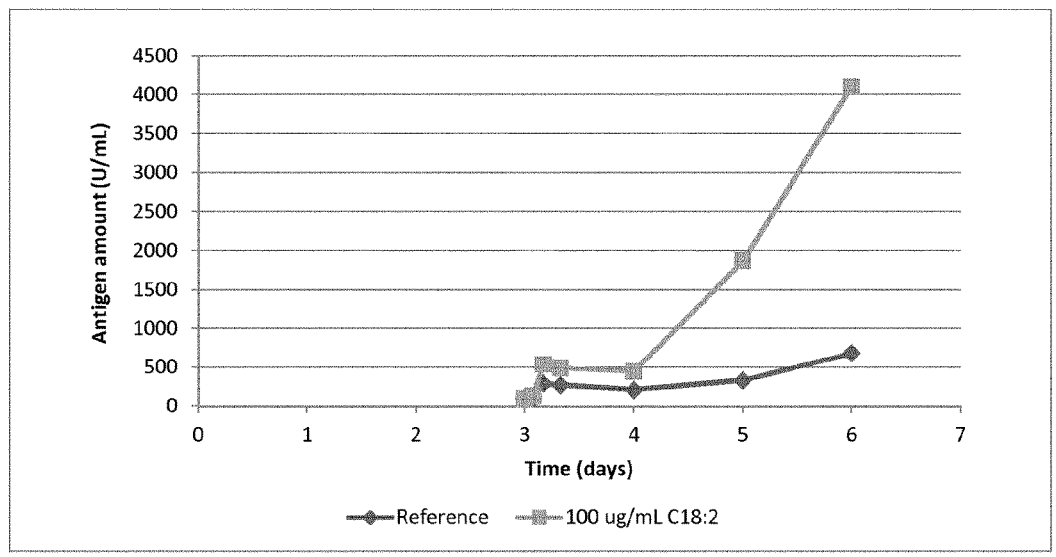

FIGS. 6 and 7:
Respectively the biomass and the antigen amount measurement results from different cultures of *Leptospira* from serogroup Sejroe (serovar Hardjo), proliferated in EMJH medium with high LA BSA; the cultures were either un-supplemented as reference culture, or supplemented with 100 µg/ml linoleic acid from pure linoleic acid in ethanol.

Figure 8:
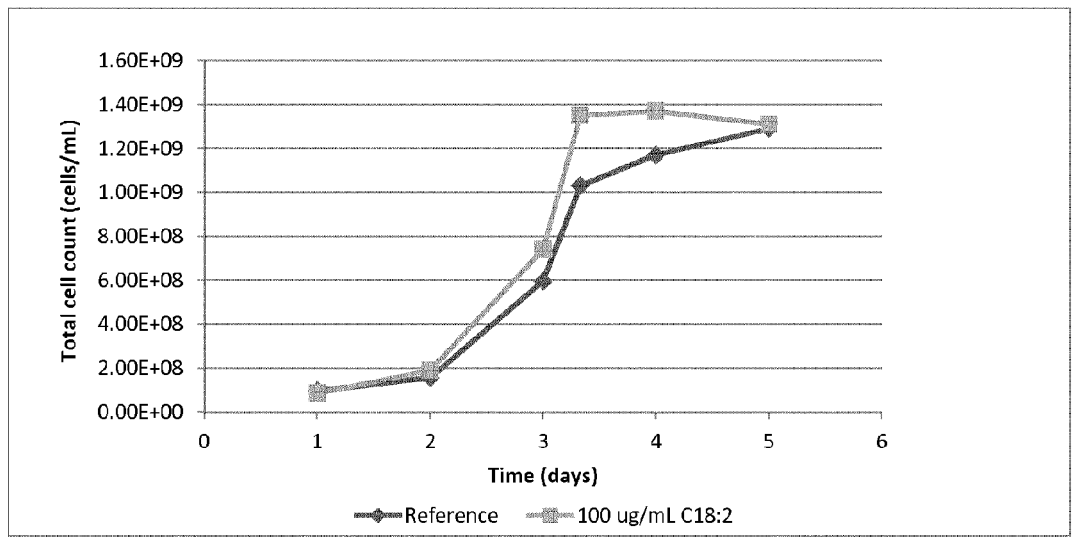
Figure 9:
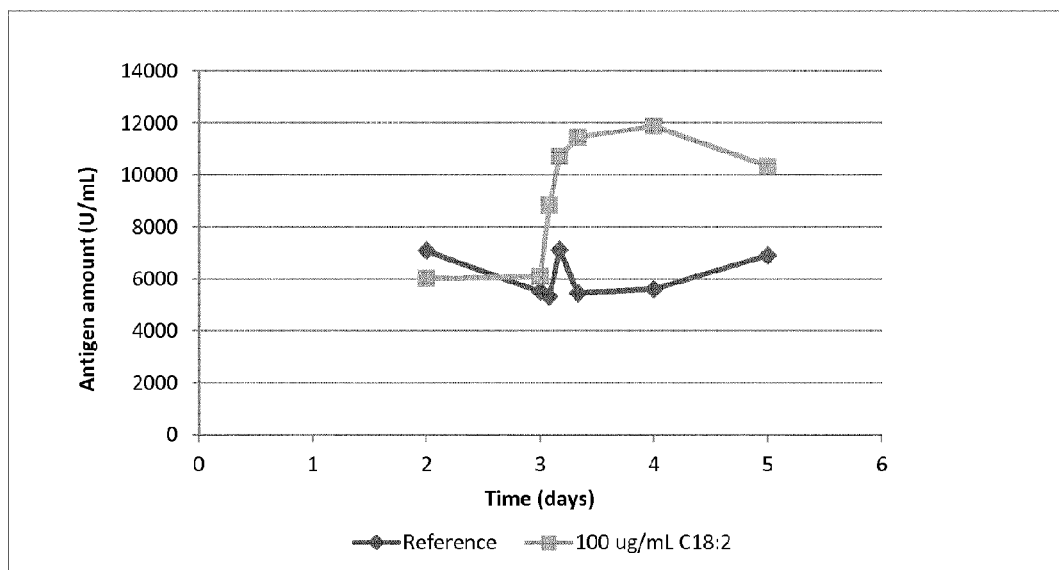

FIGS. 8 and 9:
Respectively the biomass and the antigen amount measurement results from different cultures of *Leptospira* from serogroup Grippotyphosa, proliferated in EMJH medium with high LA BSA; the cultures were either un-supplemented as reference culture, or supplemented with 100 µg/ml linoleic acid from pure linoleic acid in ethanol.

FIG. 10:
Effect on the increase in antigenic mass when a culture of *Leptospira* is supplemented at different stages of proliferation. *Leptospira* from serogroup lcterohaemorrhagiae were cultured in standard EMJH medium, and supplemented with 100 µg/ml linoleic acid, at early-, mid-, or late stage. Initial sampling was at 2, 4, and 8 hours after supplementation.

Figure 11:
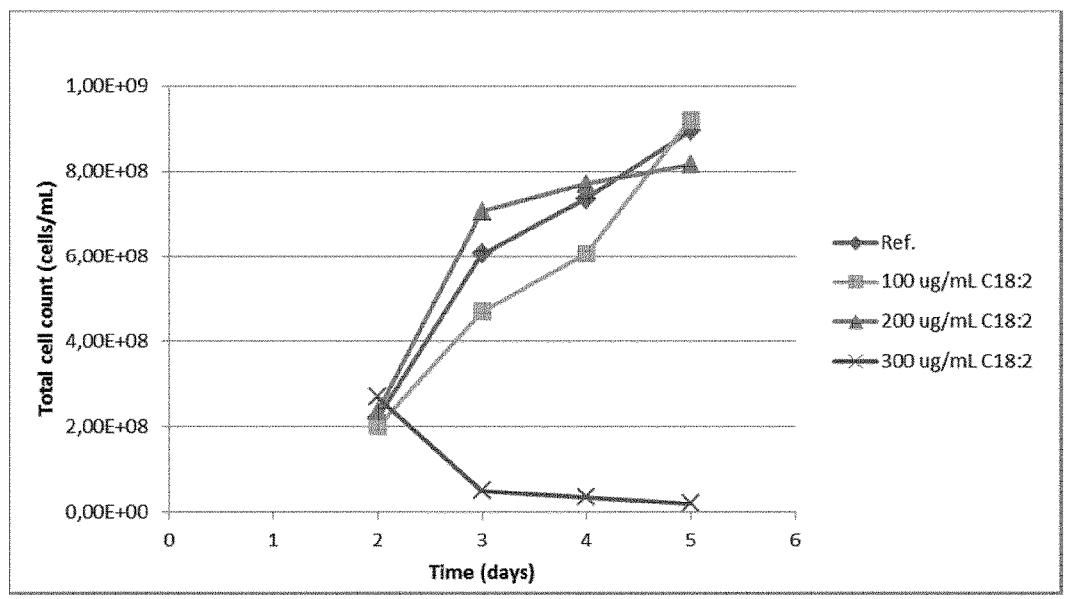
Figure 12:
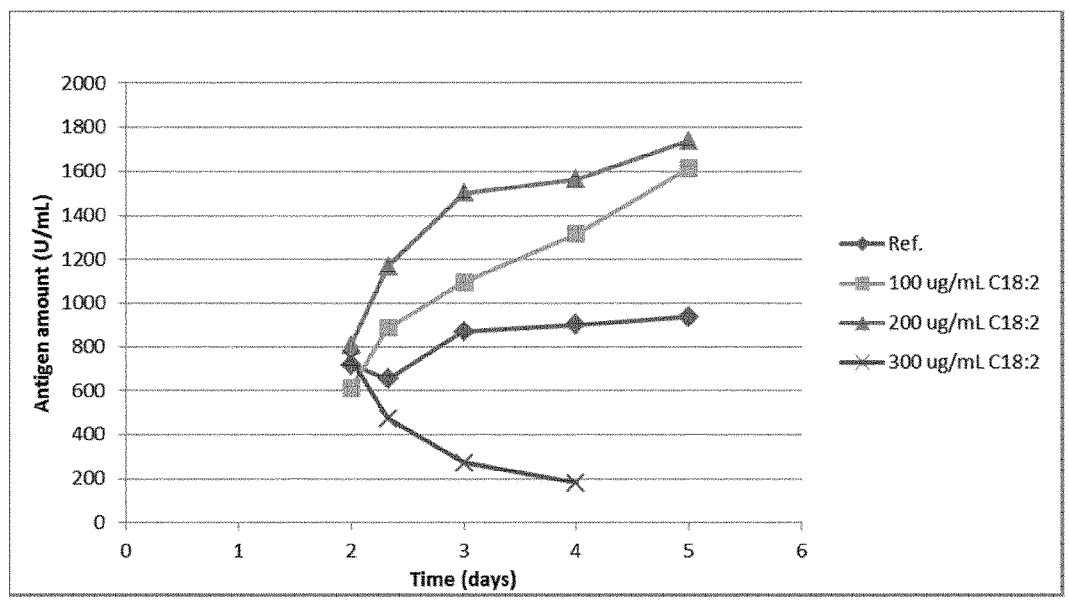

FIGS. 11 and 12:
Effects of supplementation with different amounts of linoleic acid, on biomass and antigenic mass of a culture of *Leptospira* serogroup Tarassovi, in standard EMJH medium.

Figure 13:
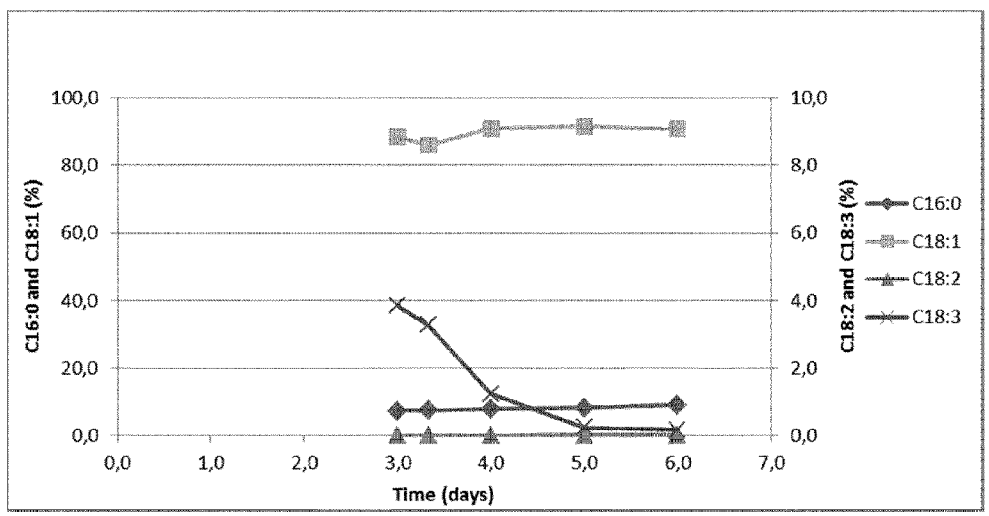

FIGS. 13 and 14:
Profile of relative fatty acid amounts in a culture of *Leptospira* serogroup lcterohaemorrhagiae in EMJH medium, over time.

FIG. 13: unsupplemented culture; NB: C18:2 and C18: 3 levels are presented relative to the right hand side vertical axis.

FIG. 14: culture supplemented with 200 µg/ml alpha C18:3.

FIGS. 15-20:
The effects of supplementation with different amounts of alpha-or gamma C18:3, on biomass and on antigenic mass of cultures of *Leptospira* serogroup lcterohaemorrhagiae in EMJH medium.

FIGS. 21-32:
The effects of supplementation with different amounts of alpha-or gamma C18:3, on biomass and on antigenic mass of cultures of *Leptospira* from different serogroups, in EMJH medium.

Figure 21:
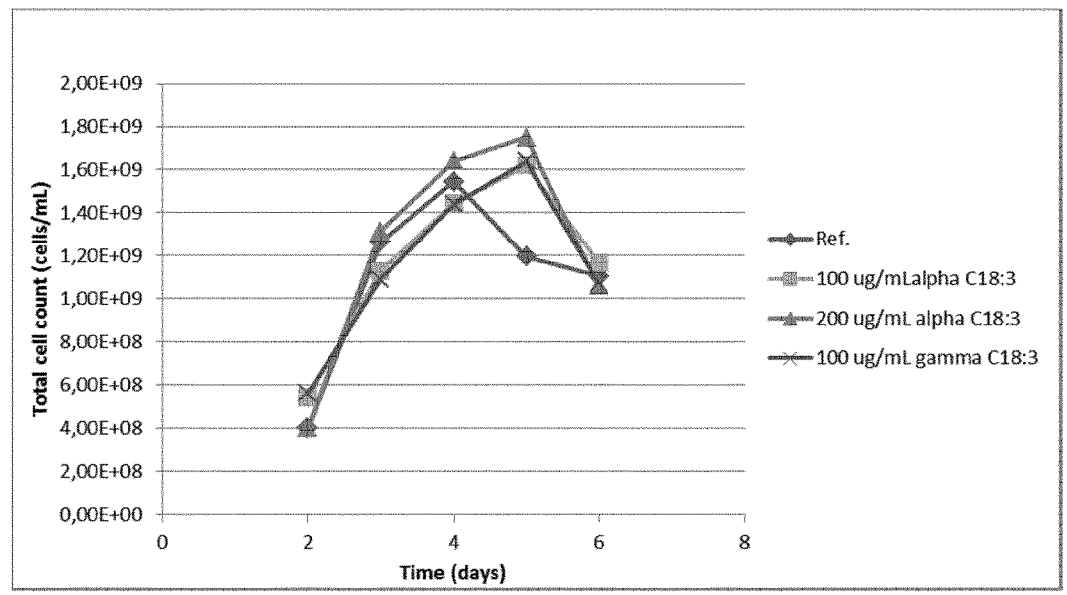
Figure 22:
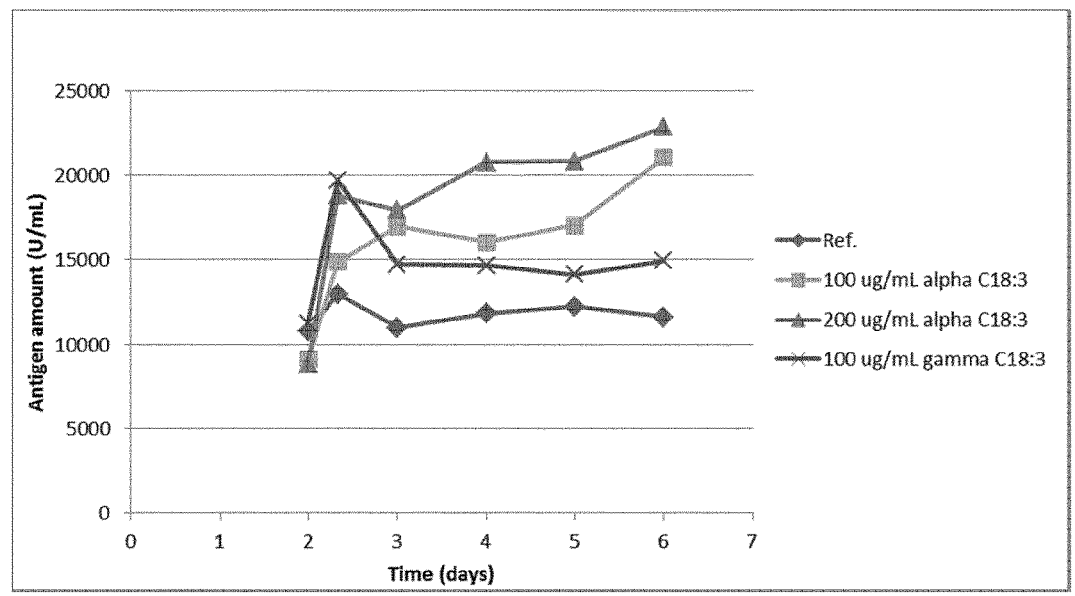
Figure 23:
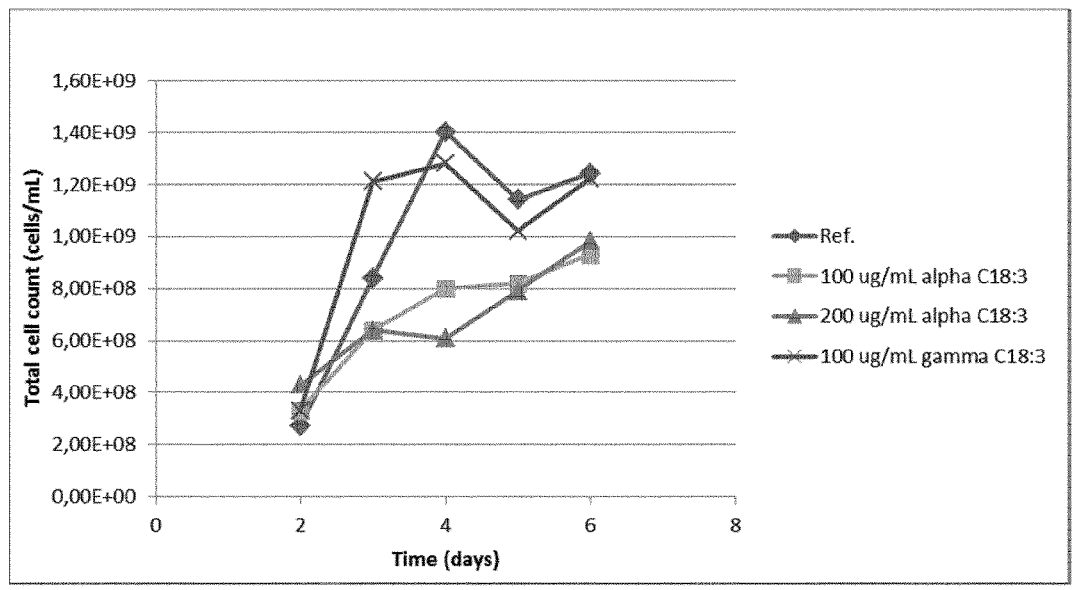
Figure 24:
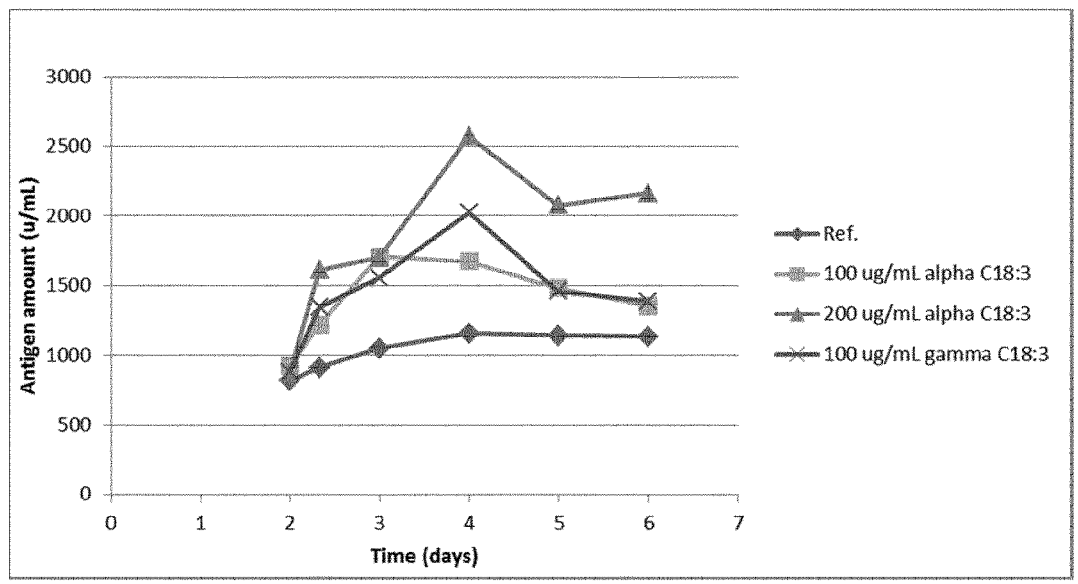
Figure 25:
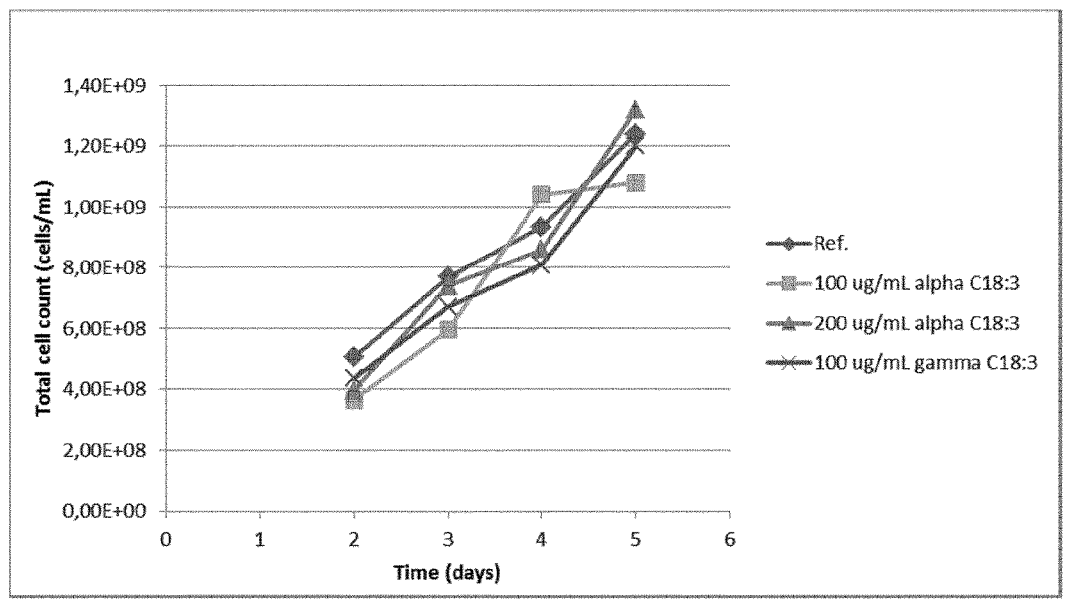
Figure 26:
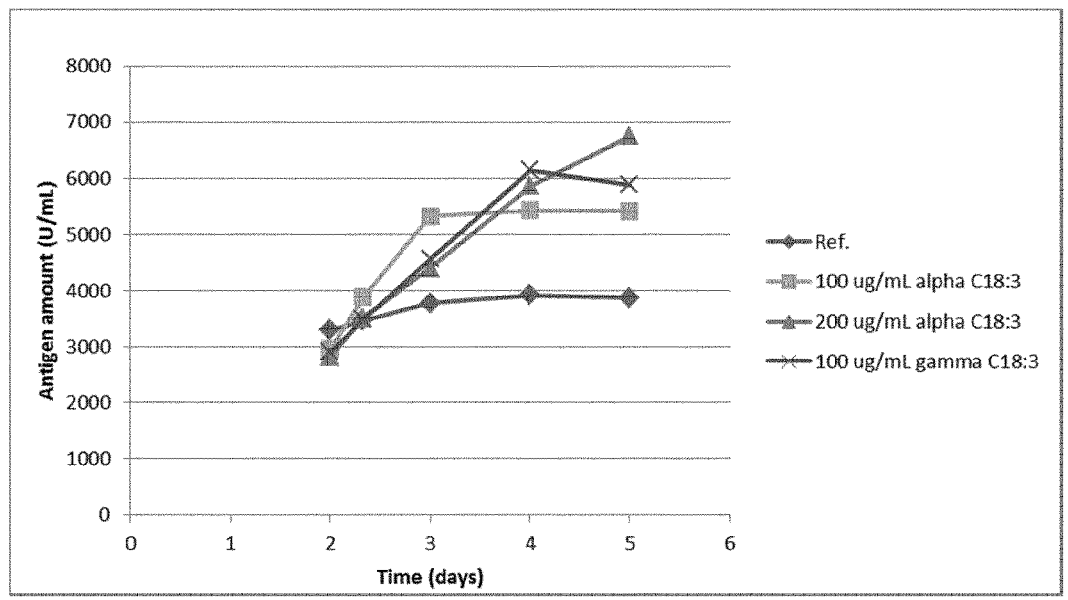
Figure 27:
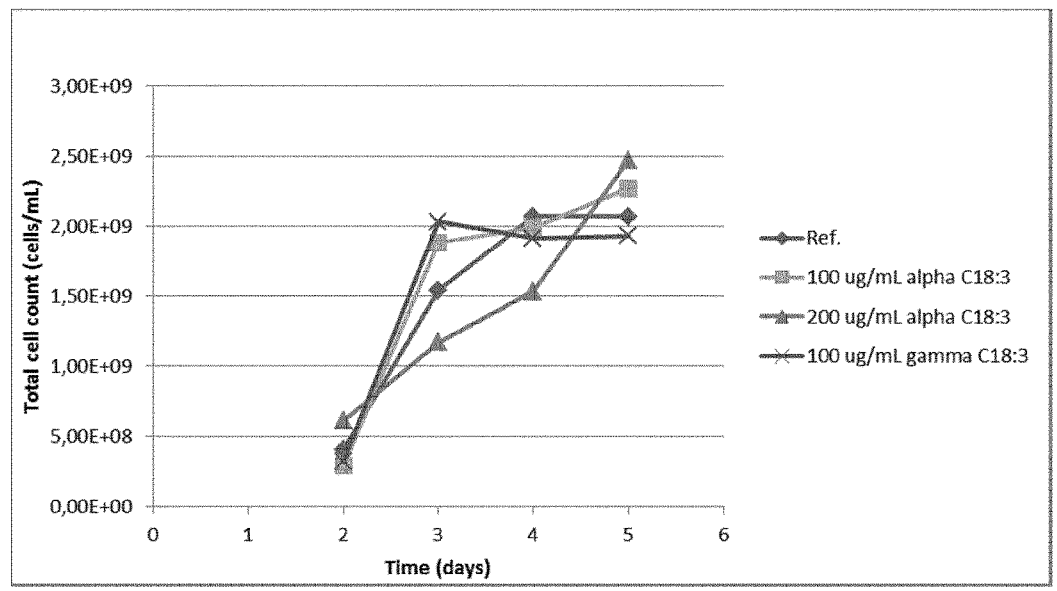
Figure 28:
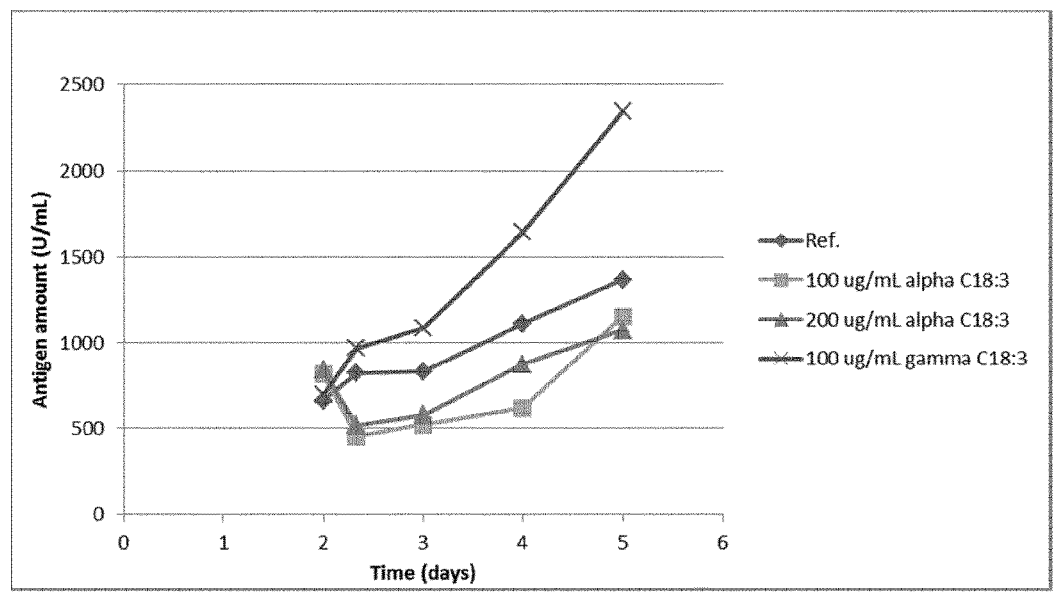
Figure 29:
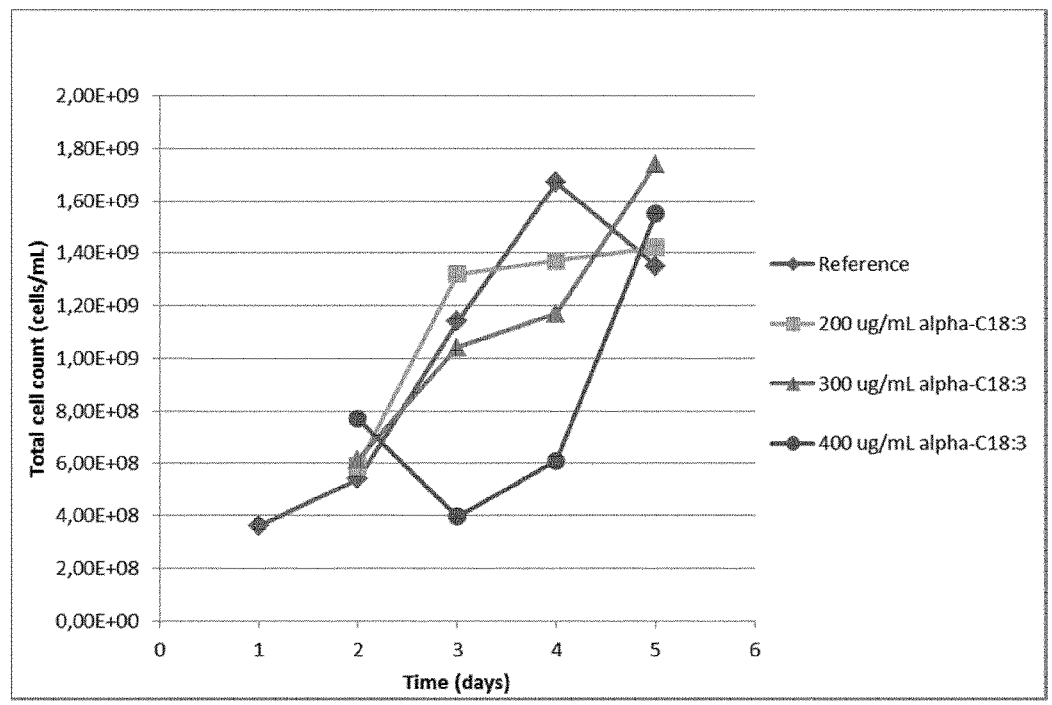
Figure 30:
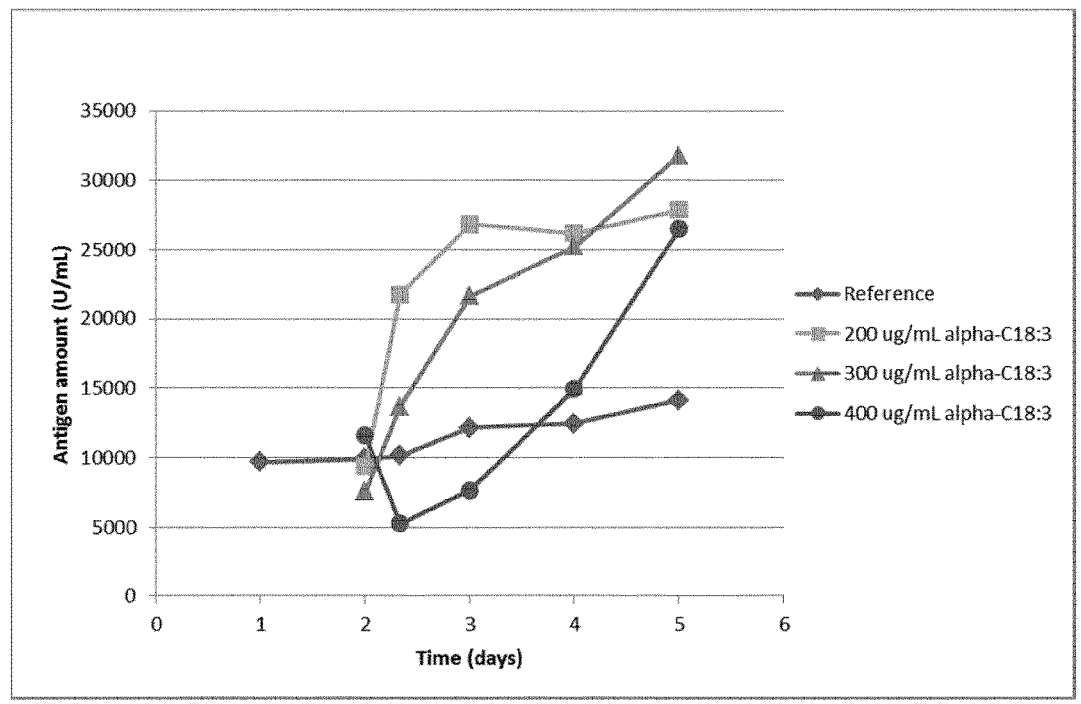
Figure 31:
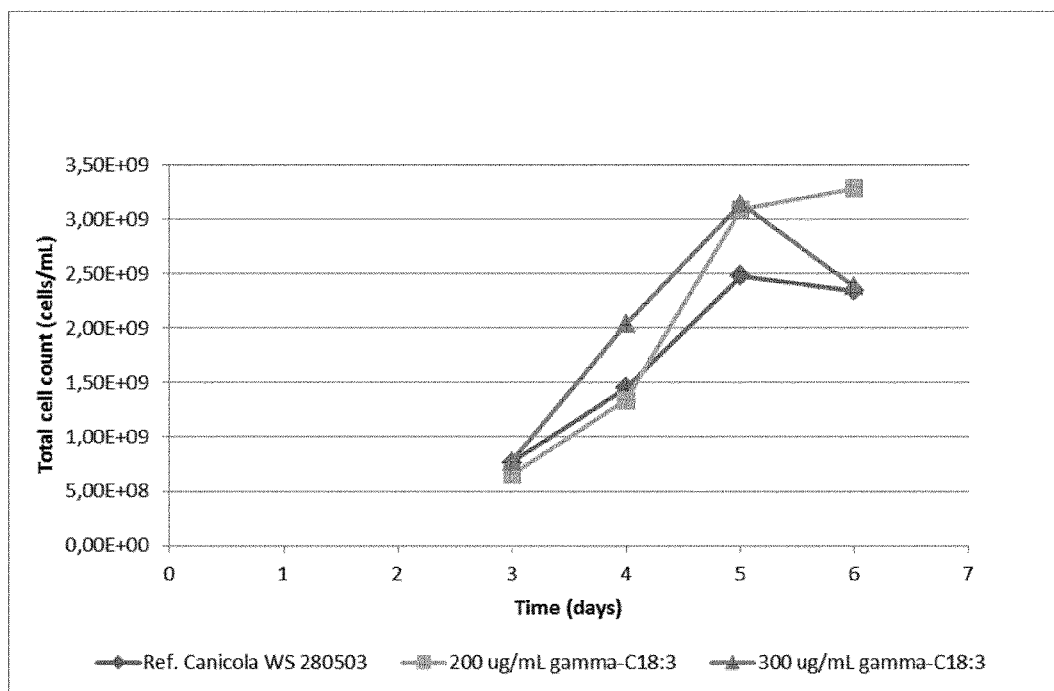
Figure 32:
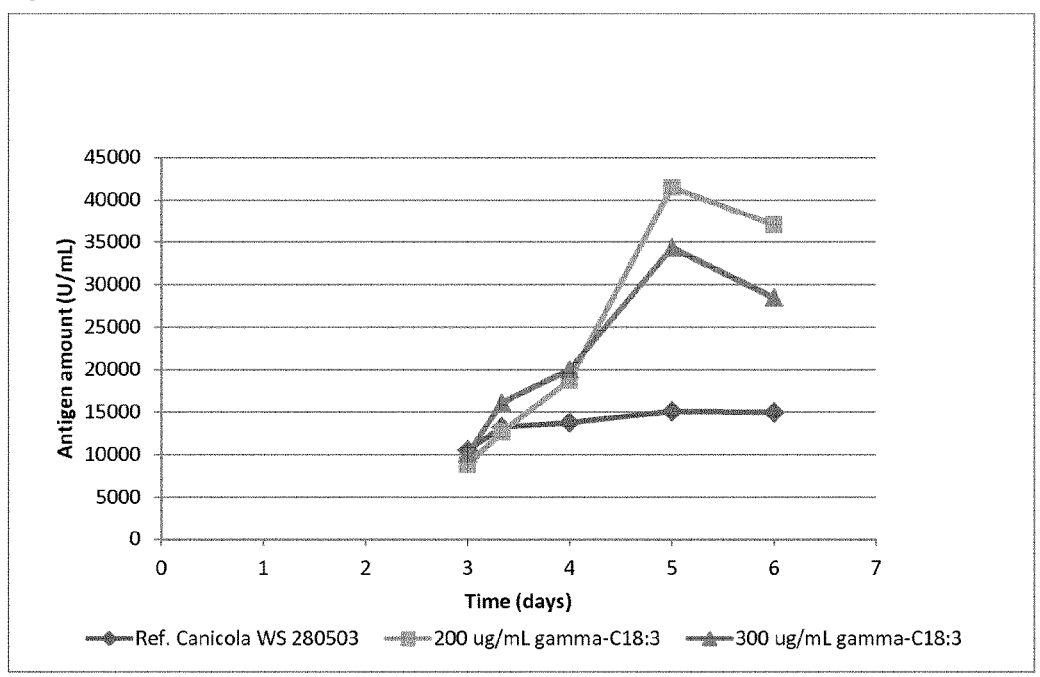

FIGS. 21 and 22: culture of *Leptospira* serogroup Australis (serovar Bratislava), FIGS. 23 and 24: culture of *Leptospira* serogroup Tarassovi, FIGS. 25 and 26: culture of *Leptospira* serogroup Grippotyphosa, FIGS. 27 and 28: culture of *Leptospira* serogroup Pomona, FIGS. 29 through 32: culture of *Leptospira* serogroup Canicola.

FIGS. 33-36:
The effects of supplementation of a culture of *Leptospira* serogroup lcterohaemorrhagiae in EMJH medium, with alpha-or gamma C18:3 at different time-points of the culture.

Figure 37:
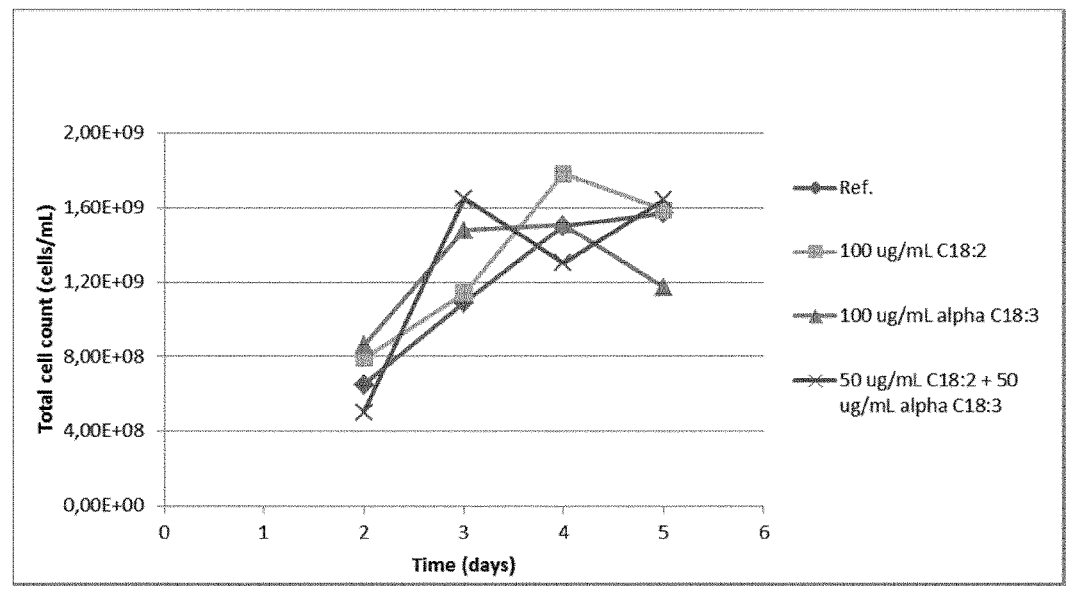
Figure 38:
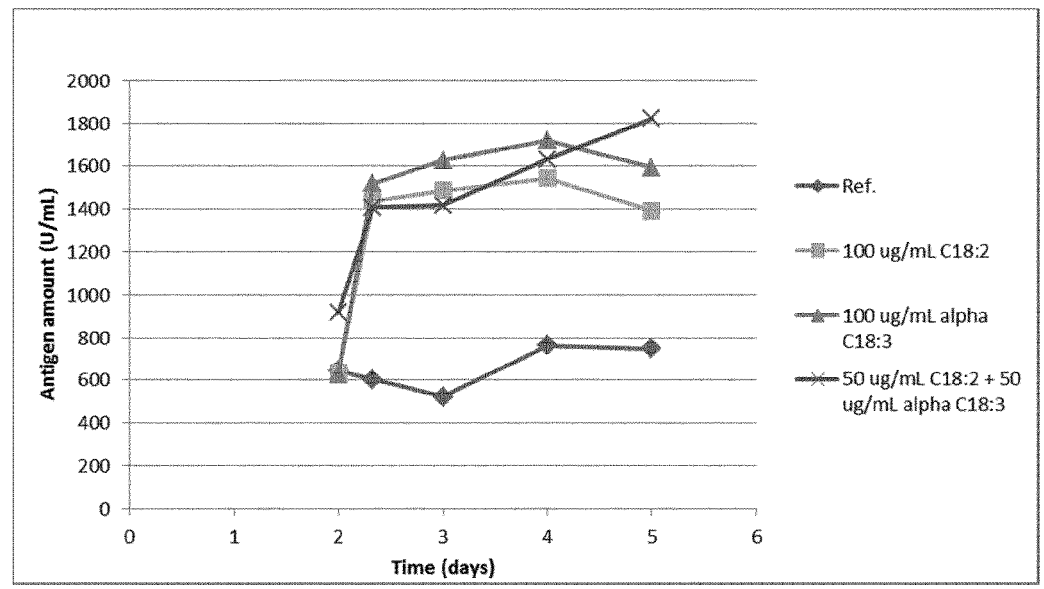

FIGS. 37 and 38:
Comparison of the effect of separate versus combined supplementation with different polyunsaturated C18 fatty acids, on the biomass and on the antigenic mass of a culture of *Leptospira* serogroup lcterohaemorrhagiae in EMJH medium.

The invention claimed is:

1. A vaccine against Leptospirosis comprising an inactivated *Leptospira* culture and a pharmaceutically acceptable carrier; wherein said inactivated *Leptospira* culture is prepared by a method for increasing the antigenic mass of a *Leptospira* culture comprising the steps of supplementing said *Leptospira* culture with at least 15 µg/ml of a polyunsaturated C18 fatty acid and inactivating said supplemented *Leptospira* culture; wherein the polyunsaturated C18 fatty acid is selected from the group consisting of linoleic acid, alpha-linolenic acid, gamma-linolenic acid, and combinations thereof; and wherein said inactivated supplemented *Leptospira* culture has an increased antigenic mass that exceeds the corresponding increase in biomass; wherein when the *Leptospira* is serogroup pomona the polyunsaturated C18 fatty acid is not alpha-linolenic acid.

2. A method for producing a vaccine against *Leptospirosis* comprising the steps of:
   a. proliferating a *Leptospira* culture in an in vitro system,
   b. supplementing said *Leptospira* culture with at least 15 μg/ml of a polyunsaturated C18 fatty acid, wherein the polyunsaturated C18 fatty acid is selected from the group consisting of linoleic acid, alpha-linolenic acid, gamma-linolenic acid, and combinations thereof, and wherein said supplemented *Leptospira* culture comprises an increased antigenic mass that exceeds the corresponding increase in biomass; wherein when the *Leptospira* is serogroup pomona the polyunsaturated C18 fatty acid is not alpha-linolenic acid,
   c. inactivating and harvesting said supplemented *Leptospira* culture, and
   d. admixing the inactivated *Leptospira* culture with a pharmaceutically acceptable carrier.

3. The method of claim 2, wherein between steps a. and b. there is an additional step selected from the group consisting of harvesting, storage, and purification, of the *Leptospira* culture.

4. The method of claim 2 wherein the polyunsaturated C18 fatty acid is comprised by a vegetable oil.

5. A method for increasing the antigenic mass of a *Leptospira* culture comprising the step of supplementing said *Leptospira* culture with a compound or composition that is relatively rich in a polyunsaturated C18 fatty acid; wherein the polyunsaturated C18 fatty acid is selected from the group consisting of linoleic acid, alpha-linolenic acid, gamma-linolenic acid, and combinations thereof; and wherein the compound or composition that is relatively rich in a polyunsaturated C18 fatty acid is a vegetable oil; wherein when the *Leptospira* is serogroup pomona the polyunsaturated C18 fatty acid is not alpha-linolenic acid.

6. The method of claim 2, wherein the polyunsaturated C18 fatty acid comprises between 25 and 250 μg/ml linoleic acid.

7. The method of claim 2, wherein the polyunsaturated C18 fatty acid comprises between 15 and 300 μg/ml linolenic acid.

8. The vaccine of claim 1, wherein the polyunsaturated C18 fatty acid comprises between 15 and 300 μg/ml linolenic acid.

9. A vaccine against Leptospirosis comprising the inactivated *Leptospira* culture of claim 7.

10. A vaccine against Leptospirosis comprising the inactivated *Leptospira* culture of claim 6.

11. A vaccine against Leptospirosis comprising the inactivated *Leptospira* culture of claim 2.

12. A vaccine against Leptospirosis comprising the inactivated *Leptospira* culture of claim 3.

13. The vaccine of claim 2, wherein said inactivating of the *Leptospira* culture to make the inactivated *Leptospira* culture is done by chemical inactivation.

14. The vaccine of claim 13, wherein the chemical inactivation is done with formalin.

15. The method of claim 5, further comprising the step of inactivating the supplemented *Leptospira* culture.

16. The vaccine of claim 1, wherein the polyunsaturated C18 fatty acid comprises 25 and 250 μg/ml linoleic acid.

17. A vaccine against Leptospirosis comprising the inactivated *Leptospira* culture of claim 15.

* * * * *